United States Patent [19]

Love et al.

[11] Patent Number: 5,446,145
[45] Date of Patent: Aug. 29, 1995

[54] POLYCHELANT COMPOUNDS

[75] Inventors: David B. Love, Campbell; William C. Dow, Fremont; Richard J. Himmelsbach, Pleasanton; Alan D. Watson, Campbell; Scott M. Rocklage, Los Gatos, all of Calif.

[73] Assignee: Nycomed Salutar, Inc., Sunnyvale, Calif.

[21] Appl. No.: 86,996

[22] Filed: Jul. 7, 1993

Related U.S. Application Data

[62] Division of Ser. No. 468,107, Jan. 19, 1990, Pat. No. 5,281,704.

[51] Int. Cl.6 .................................................. C07D 225/02
[52] U.S. Cl. ................................................. 540/465; 540/474
[58] Field of Search .............. 530/405; 536/17.1, 17.4, 536/17.9; 540/465, 474; 544/69, 168, 169; 560/169; 562/565

[56] References Cited

U.S. PATENT DOCUMENTS

| | | | |
|---|---|---|---|
| 3,859,337 | 1/1975 | Herz et al. | 260/500.5 H |
| 4,678,667 | 7/1987 | Meares et al. | 429/9 |
| 4,826,673 | 5/1989 | Dean et al. | 424/9 |
| 4,885,363 | 12/1989 | Tweedle et al. | 540/474 |
| 5,011,925 | 4/1991 | Rajagopalan et al. | 562/565 |

FOREIGN PATENT DOCUMENTS

| | | | |
|---|---|---|---|
| 186947 | 7/1986 | European Pat. Off. | |
| 0255471 | 2/1988 | European Pat. Off. | 257/2 |
| 0287465 | 10/1988 | European Pat. Off. | 257/2 |
| 0299795 | 1/1989 | European Pat. Off. | 101/26 |
| 0305320 | 10/1989 | European Pat. Off. | 101/26 |
| 8807521 | 10/1988 | WIPO | 101/26 |

OTHER PUBLICATIONS

Gries et al. Chemical Abstract 109(1): 6552X, 1988.
Benjamini et al. "immunology, a Short Course" 2nd Ed. (New York). Wiley and Sons 1991 pp. 38–43.
Konings et al. Inorg. Chem. 1990 29, 1488–1491.
Meares et al. "Chemical Abstract" vol. 111, 1989, Abstract 53304v.

*Primary Examiner*—Mukund J. Shah
*Assistant Examiner*—Y. N. Gupta
*Attorney, Agent, or Firm*—Lyon & Lyon

[57] ABSTRACT

There are disclosed polychelant compounds, that is multi-site metal chelating agents, and chelates formed therewith. The polychelants and especially their paramagnetic metal, heavy metal or radioactive metal polychelates are particularly suitable for use in diagnostic imaging, heavy metal detoxification or radiotherapy. The polychelants have a linear or branched oligomeric structure comprising alternating chelant and linker moieties bound together by amide or ester moieties the carbonyl groups whereof being adjacent the chelant moieties, each polychelant comprising at least two said chelant moieties capable of complexing a metal ion.

13 Claims, No Drawings

POLYCHELANT COMPOUNDS

This is a division of application Ser. No. 07/468,107, filed Jan. 19, 1990 now U.S. Pat. 5,281,704.

FIELD OF THE INVENTION

This invention relates to polychelants, that is multi-site metal chelating agents, and chelates formed therewith, as well as to their preparation, compositions containing them and their use, especially in medicine, in particular in diagnostic imaging. The invention relates especially to the use of metal chelates of such polychelants as contrast agents in X-ray imaging and Magnetic Resonance Imaging (MRI).

BACKGROUND OF THE INVENTION

Contrast agents may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging the contrast agents function by modifying the X-ray absorption characteristics of the body sites in which they distribute; magnetic resonance contrast agents generally function by modifying the characteristic relaxation times $T_1$ and $T_2$ of the nuclei, generally water protons, from the resonance signals of which the images are generated; and ultrasound contrast agents function by modifying the speed of sound or the density in the body sites into which they distribute.

The X-ray contrast agents first developed, barium sulfate and sodium iodide, have been superseded by iodinated organic compounds, in particular triiodophenyl compounds. Improvements in systemic toxicity over the last 40 years have also been achieved by the development of non-ionic iodinated X-ray contrast agents (see Shaw in "Radiopaques", CRC Handbook of Vitamins, Hormone and Radiopaques, CRC Press, p. 229-243). More recent improvements have come from the development of the so-called dimer X-ray contrast agents, compounds containing two triiodophenyl moieties per molecule (see McClennan in Introduction to Supplement in Investigative Radiology, 19; S289-S292 (1984)).

As the X-ray absorption cross-sections of the elements generally increase with increasing atomic number and as such cross-sections are dependent on the wavelength of the X-rays there has been some desire to utilize the X-ray absorption properties of the lanthanides and other high atomic number metals to develop contrast agents with improved X-ray attenuation especially at the wavelengths used in CT; however these attempts have generally been relatively unsuccessful.

Thus, for example, Nalbandian et al. (see Ann. N.Y. Acad. Sci. 78: 779 (1959)) and Shapiro et al. (see Ann. N.Y. Acad. Sci. 78: 756 (1959)) proposed the use of the diethylenetetraaminepentaacetic acid (DTPA) chelate of bismuth (BiDTPA) and the ethylenediaminetetraacetic acid (EDTA) chelate of lead (PbEDTA) as radiographic contrast agents but encountered problems of solubility and toxicity. In U.S. Pat. No. A-4,176,173 Winchell et al. described the use of simple hafnium or tantalum complexes as X-ray contrast agents and more recently, ytterbium DTPA has been studied as an intravascular X-ray contrast agent, and an $LD_{50}$ of 10 mmoles/kg has been reported (see Unger et al. Invest. Radiol. 21:802 (1986)).

In MRI, the use of paramagnetic metal ions, such as Mn(II), as contrast agents was first proposed by Lauterbur et al. in 1978 (see pages 752-759 in "Electrons to Tissues—Frontiers of Biological Energetics" Vol. 1, edited by Dutton et al., Academic Press, N.Y., 1978) and more recently Schering AG in U.S. Pat. No. A-4,647,447 proposed the use of salts of gadolinium(III) chelates of DTPA.

In order to achieve tissue-specific MRI contrast enhancement or to enhance relaxivity the coupling of paramagnetic chelates, such as GdDTPA, or metal complexing groups to macromolecular carriers or biomolecules, such as polysaccharides, proteins, antibodies, liposomes, enzymes, polyethyleneimines etc. has been proposed by several researchers—see for example EP-A-130934 (Schering), EP-A-136812 (Technicare), EP-A-184899 (Nycomed), EP-A-186947 (Nycomed), EP-A-277088 (Schering), EP-A-305320 (Schering), WO-A-88/07521 (Schering), WO-A-88/08422 (Schering), WO-A5/05554 (Amersham), WO-A-89/06979 (Nycomed), EP-A-331616 (Schering) and Schmiedl et al. Radiology 162:205 (1987). Furthermore, WO-A-88/01178 (Dow) discloses attempts made to chelate metal ions with carboxylate-terminal "starburst dendrimers" and to conjugate antibodies to such dendrimers, however the therapeutic or diagnostic utility of such structures has not been established.

The visualization of certain disease states such as cancer can benefit particularly from the use of tissue targeting contrast agents. Thus for example, in MRI it may be necessary to deliver 100-1000 paramagnetic centres to a tumour to obtain sufficient relaxation enhancement for visualization. Macromolecular polychelates for use in this regard have been proposed but attempts to prepare such macromolecular polychelates and then to attach them to target-specific proteins such as antibodies have not met with great success (see for example Manabe et al. in Biochimica et Biophysica Acta 883:460 (1986) and Schreve et al. in Magnetic Resonance in Medicine 3: 336 (1986)).

Thus, a need still remains for alternative contrast agents with reduced toxicity, enhanced contrast characteristics and/or modified biological properties and, more especially in the field of X-ray contrast agents, significant opportunity exists for improvement in the reduction of contrast media cost and toxicity, in the reduction of patient discomfort and in the reduction of the incidence of side reactions, enzymatic deiodination, etc.

The disclosures of each of the publications and other documents referred to above, as well as each of those referred to hereinafter, are incorporated by reference in the present specification.

SUMMARY OF THE INVENTION

We have now found that metal, e.g. heavy metal or paramagnetic metal, chelates of a range of novel oligomeric polychelants are particularly suited to use as imaging contrast agents, and especially, in the case of heavy metal chelates, as X-ray contrast agents.

Thus viewed from one aspect the invention provides a linear or branched oligomeric polychelant comprising alternating chelant and linker moieties bound together by amide or ester moieties the carbonyl groups whereof being adjacent the chelant moieties, said polychelant comprising at least two said chelant moieties capable of complexing a metal ion, or a salt or chelate of a said polychelant.

The invention thus particularly provides metal chelates which are the chelate complexes of polychelants according to the invention and metal ions, preferably at least two metal ions.

The novel oligomeric polychelants and the metal chelates and polychelates formed therefrom are useful in a variety of biomedical contexts including magnetic resonance imaging, X-ray/CT imaging, nuclear medicine and heavy metal detoxification in mammals. The polychelants comprise a multiplicity of chelating sites whereby more than one metal ion may be complexed to a single molecule. The resulting novel oligomeric metal chelate complexes have many properties which make them particularly advantageous, such as relatively low toxicity, beneficial imaging properties and distinctive biodistribution characteristics.

A direct relationship exists between the concentration of an X-ray attenuator and its efficacy in contrast enhancement. This concentration versus contrast effect relationship is not linear with respect to MRI contrast agents where a threshold concentration of the paramagnetic entity is required to affect the proton relaxation rates in a physiologic region that is being imaged and so enhance contrast. Beyond this threshold concentration, any further increase in concentration results in little improvement in contrast enhancement. Thus a primary benefit of the oligomeric polychelates for MR applications lies in the ability to lower the threshold dosage of contrast agent (and hence the toxicity) required for enhancement. The biodistribution and pharmacokinetic properties of the polychelates may also differ advantageously from those of monomeric chelate contrast agents.

As used herein, the term "oligomeric polychelant" refers to chelants capable of chelating more than one metal ion, i.e. comprising more than one chelating site, as compared for example to the monomeric "monochelants" such as DTPA or EDTA which have only one chelating site per molecule. The multiple chelating sites in the polychelahts of the invention are capable of complexing metal ions, and in particular paramagnetic metal ions (e.g. of atomic number 21 to 29, 42, 44 and 57 to 71, especially 24 to 29 and 62 to 69), heavy metal ions (e.g. of atomic number 37 or more preferably 50 or more) and ions of radioactive metal isotopes.

For use in diagnostic imaging, radiotherapy or heavy metal detoxification, the polychelants of the invention are advantageously used to chelate lanthanides (e.g. La, Ce, Pr, Nd, Pm, Sm, $^{153}$Sm, Eu, Gd, Tb, Dy, Ho, Er, Tm, Yb, and Lu) and other metal ions such as, for example, Mg, Ca, Sc, Ti, V, Cr, Mn, Fe, Co, Ni, Cu (e.g. $^{64}$Cu or $^{67}$Cu), Zn, Ga, Sr, Y, Zr, Tc, Ru, In, Hf, W, Re, Os, Pb and Bi, including isotopes and radioisotopes thereof, especially $Eu^{3+}$, $Gd^{3+}$, $Dy^{3+}$, $Ho^{3+}$ and $Yb^{3+}$. Particularly preferred radioisotopes include $^{153}$Sm, $^{64}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi and $^{214}$Bi.

Because the polychelants of the invention comprise a multiplicity of chelating sites, the chelate complexes formed therewith may include more than one metal ion. For MRI or X-ray and ultrasound applications the chelates of the invention preferably comprise, per molecule, two or more complexed paramagnetic metal ions or heavy metal ions respectively. In one generally preferred embodiment, the chelated metal ions are of the same element and isotope; however in other preferred embodiments the polychelant may be used to chelate ions of two or more different metal elements or isotopes. In this way, for example, the X-ray cross section of a contrast agent can be matched to the X-ray spectrum used for radiographic investigation by selecting a polychelate comprising ions of two or more different heavy metals.

Similarly, it is known that heavy metal chelate toxicity may be reduced by inclusion of chelated calcium or other relatively weak chelate complex forming ions within an MRI contrast medium (see U.S. Ser. No. 07/249,745, 249,746, 314,729, 317,222, 378,776 and 386,807 of Cacheris and Quay and EP-A-270483 (Schering)) and one or more of the chelant sites in a polychelate according to the invention may be used to chelate calcium or other physiologically tolerable, weak complex forming metal ions.

The ability to incorporate a plurality of metal ions in a single molecule results in the polychelates according to the invention, on a molar basis, being able to exhibit greater response in in vivo applications such as magnetic resonance imaging, X-ray/CT, nuclear medicine, and the like. Similarly, in heavy metal detoxification each polychelant molecule or weak complex thereof will be capable of removing more than one toxic metal ion from the body, thus increasing the molar efficacy of the treatment.

Due to the increased number of chelation sites on the polychelant compounds of the invention compared to monochelants a lower molar dosage may be used to achieve the same level of metalchelation. Since chelate toxicity is dependent on factors such as the degree to which the chelated metal ion is released in vivo, the effects on plasma ion concentrations of the non-complexed or weakly complexed chelant sites, specific chemotoxic effects of the metal chelate complex and the number of particles (osmolality), this decreased dosage can result in a reduction in toxicity in view of, for example, decreased metal ion release, reduced unwanted plasma ion concentration distortion, decreased osmolality etc.

In addition, the relatively high molecular weights of the polychelant and polychelates of the invention as well as their ability to be coupled to functional substituents (such as plasma proteins, antibodies or antigens) allows selection of appropriate biodistribution characteristics and permits tissue or organ targetting, i.e. preferential delivery to such tissue material as tumours. This in turn will result in improved imaging characteristics, e.g. better selectivity, contrast/noise ratio, imaging time, and the like.

Additional benefits of the present invention will be apparent from the following detailed description.

DETAILED DESCRIPTION OF THE INVENTION

In illustrating the molecular structure of the oligomeric polychelants and polychelates of the invention, the individual chelant moiety will be designated most generally by the symbol "A". Such chelant moieties may be chosen from those known in the art to be capable of complexing metal ions, and include, for example, the residues of polyaminopolycarboxylic acids (PAPCAs) and derivatives thereof, e.g. diethylenetriaminepentaacetic acid (DTPA), 1,4,7,10-tetraazacyclododecanetetraacetic acid (DOTA), 1-oxa-4,7,10-triazacyclododecanetriacetic acid (OTTA), 1,4,7,10-tetraazacyclododecanetriacetic acid (DO3A), ethylenediaminetetraacetic acid (EDTA), triethylenetetraaminehexaacetic acid (TTHA), 1,4,8,11-tetraazacyclotetradecanetetraacetic acid (TETA), and trans-1,2-diaminocyclohexane-N,N,N',N'-tetraacetic acid (DCTA). Derivatives of such chelants, for example their amides and esters, especially optionally hydroxylated $C_{1-18}$ alkyl-amides or -esters are also appropriate and often preferred chelants, as will be described in detail below.

Many PAPCAs are known and have been suggested in the literature for use for example as chelants in paramagnetic MRI contrast agents or as heavy metal detoxification agents. In this regard, besides those compounds mentioned above, particular reference may be had to the PAPCAs disclosed or discussed in EP-A-71564, EP-A-130934, DE-A-3401052, EP-A-230893, EP-A-232751, EP-A-292689, EP-A-255471, EP-A-287465, U.S. Pat. No. A-4,687,659, WO-A-89/06979 and WO-A-89/00557 and the documents referred to therein.

For sake of clarity, the symbol A is used herein to designate the chelant moiety whether chelated to a metal ion M or not, whether deprotonated (or otherwise ionized) or not, and whether singly or multiply attached to linker moieties.

The symbol "L" is used herein to designate a linker moiety which may be singly or multiply attached to chelant moieties.

The polychelants of the invention will contain at least two A moieties and at least one L moiety, preferably a total of up to 100 such moieties in all, especially preferably 3 to 20, particularly 3 to 10.

An important aspect of the invention is that the chemical bond between each chelant moiety A and its adjacent linker moiety (or moieties) L comprises an amide or ester linkage with the carbonyl group adjacent the chelant moiety.

Thus the bonds A—L in the polychelant or polychelates of the invention will generally be of the formula $$A'—CO—X—L'$$

where A'CO and L'X respectively are A and L and X is oxygen or a secondary, tertiary or ring nitrogen.

X is preferably attached to a carbon of L'.

In one preferred embodiment of the invention the polychelant/polychelate has the basic backbone structure

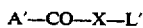   (I)

where "a" is a positive integer, each A may be the same or different, each L may be the same or different and each mid-chain A or L moiety may optionally carry at least one straight or branched oligomeric side chain.

Where X is a secondary nitrogen, one or both (but preferably one) of the X-attached portions of L may serve to link the chelant moieties of the oligomer. Non-linking X-attached groups are preferably groups R' where R' is selected from hydrogen, hydrocarbon groups such as for example alkyl, cycloalkyl, alkenyl, alkynyl and aryl groups optionally substituted by hydroxyl, amine and carboxyl groups and derivatives thereof and other suitable groups; carbohydrate groups; peptide residues; polypeptides; proteins; and other biomolecules.

The linker moieties in the compounds of the invention may, as indicated above, each serve to link together two or more chelant moieties, thereby holding together the multiple chelating site structure that is characteristic of the compounds of the invention. Besides filling this role as linker, or spacer, of chelant sites, the linker moiety can be so selected as to yield a product having other desired characteristics. Thus for example it is possible to increase hydrophilicity, lipophilicity or tissue specificity of the end product by attaching to or incorporating within linker moieties groups which are hydrophilic, lipophilic or tissue targetting. To achieve a desired balance between overall molecular weight and number of chelant sites per molecule, the length or molecular weight of the linker moiety may be selected appropriately.

Moreover, for the end product to be readily characterized, i.e. for the different molecules within a given sample to be relatively uniform, readily characterizable precursors for the linker moieties may be used. Preferably the overall molecular weight of the linker moieties, excluding any pendant macromolecules or biomolecules will be less than 1000, most particularly less than 500 and especially less than 150. In order to achieve a relatively high chelated metal ion density within the polychelates of the invention, mid-chain linker moieties will preferably provide a chain of up to 22, preferably up to 12, especially up to 10 and particularly 3 to 8, atoms in length between the carbonyl carbons of the amide or ester bonds to adjacent chelant moieties. The terminal atoms of such chains will of course be oxygen or nitrogen, although preferably both will be nitrogen, and mid chain atoms will preferably be carbon although other mid chain atoms such as nitrogen, phosphorous, boron, silicon and oxygen may occur. Excluding terminal oxygens and nitrogens therefore, the linker moieties will preferably be optionally unsaturated, optionally substituted, optionally carbocyclic or heterocyclic ring containing, linear or branched hydrocarbon groups, e.g. oxa, aza, hydroxy, amino, carboxyl, cycloalkylene (e.g $C_5$ to $C_7$ cycloalkylene) or arylene (e.g. $C_6$ to $C_{10}$ arylene) substituted alkylene, alkenylene or alkynylene groups.

It will frequently be useful to utilize di- or polyamino linker moieties L, as for example in structures of the form . . . A—L—A . . . , where the bonding exemplified by the structure

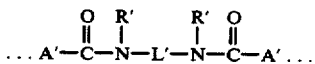

where each R' is as defined above.

The amide linkages depicted above are particularly advantageous in that the carbonyl group being adjacent the chelant moiety is potentially able to contribute to the metal coordination effect and thereby increase the stability of the resultant complex. This carbonyl portion of the amide linkage may be derived from, for example, a carboxylate group in a precursor PAPCA. Such polychelants may be synthesized in high yields, for example using standard techniques e.g. as described below, from relatively inexpensive starting materials, such as PAPCAs and polyamine linker compounds, with minimal need for selective protection of functional groups on the chelants.

In one preferred embodiment of the invention, each linker moiety, which may be the same or different, is a group $L''X_i$ where X is as hereinbefore defined, i is a positive integer, preferably 2, 3 or 4, and L'' is a branched or linear, substituted or unsubstituted, hydrocarbon group, such as an alkylene, cycloalkylene, alkenylene, alkynylene or arylene group, preferably containing from 1 to 20 carbons and most preferably 1 to 6 carbons, or a combination of two or more such groups or L″$X_i$ is a polyalkylamine residue (such as —NH($CH_2CH_2NH$—)$_j$, j being preferably 1 to 20), or an aminopolyether or aminopolyalcohol residue (such as an aminopolyethyleneglycol residue) preferably containing from 4 to 20 carbons and most preferably 4 to 8 carbons, or an aminocarbohydrate residue, or an aminofatty acid residue or the residue of another compound capable of forming an amide or ester linkage with two or more chelant moieties (with any substitutent preferably being chosen to enhance solubility or biodistribution of the resultant compound, such as —OH, —$NH_2$ or —$CO_2H$, a peptide residue, a polypeptide or protein such as a plasma protein, antibody or antigen, or other suitable moiety).

The oligomeric polychelants and the chelate complexes of the invention include a wide variety of structures wherein a multiplicity of chelant moieties A are linked to one another through one or more linker moieties. In one general embodiment of the present invention, the oligomeric polychelant is of the formula II

(II)

wherein b is zero or a positive integer (preferably 1,2,3,4 or 5); each L is independently selected from the groups L herein defined; and each A is independently a chelant moiety capable of complexing a metal ion. The chelant moieties A may be the same or different, and each linker moiety L may be the same or different. Each chelant moiety A is covalently bonded, preferably by an amide bond, to one or more adjacent linking groups, which linker moieties in turn link the individual chelant moieties A to one another to form the polychelant.

In one preferred embodiment, the chelant moieties A will be derived from or related to the same mono-chelant. It is also frequently convenient to utilize the same linker moiety L in each required linking position.

Preferred linker compounds useful for the production of the oligomeric compounds described herein include, but are not limited to, polyamino compounds such as the following
1,2-diaminoethane,
1,3-diaminopropane,
1,4-diaminobutane,
1,5-diamino-3-(2-aminoethyl)-pentane,
N,N′-dimethyl-1,2-diaminoethane,
N,N′-dimethyl-1,3-diaminopropane,
2-hydroxy-1,3-diaminopropane,
2-amino-1,3-diaminopropane,
2,3-diamino-1,4-butanediol,
1,4-diamino-2,3-butanediol,
1,4-diaminocyclohexane,
1,4-phenylenediamine, and especially
1,1,1-tris(aminomethyl)ethane,
2,2′,2″-triaminotriethylamine,
tris-(aminomethyl)methane,
diethylenetriamine,
triethylenetetraamine,
1,3,5-triaminocyclohexane, and
1,3,5-phenylenetriamine.

Where X in L′X is oxygen, it is frequently preferable to choose a bulky, as for example a branched, L′ in order to increase the stability of the resulting ester bond against hydrolysis. In this regard, preferred linker compounds include, but are not limited to, polyhydroxy compounds such as the following
2,2-dimethyl-1,3-propanediol,
tris(2-hydroxyethyl)amine,
1,1,1-tris(hydroxymethyl)ethane, and
tris(hydroxymethyl)aminomethane.

The synthetic methods described herein allow the use of linker compounds such as the foregoing to produce oligomeric polychelants of highly defined structure and size. By selecting linker moieties of specific structure, polychelant/polychelate compounds are produced that are relatively stable against hydrolysis in vivo as compared to protein or polypeptide based chelates. Moreover, the cost of starting materials useful in forming the linkages described is much lower than, for example, that of a homopolypeptide backbone.

The compounds of formula II may be termed "linear" oligomeric polychelants. As mentioned earlier however the present invention also embraces compounds which may be termed "branched" e.g. compounds having the backbone structure A(LA)$_a$ (as mentioned above) wherein one or more of the backbone "monomer" residues A and L is a branching site. Thus for example the polychelant compounds of the invention include simply and multiply branched oligomers which are for example compounds of formula III

(III)

where a is a positive integer; c is zero or a positive integer, preferably 1 to 5; d is zero or a positive integer, preferably 1 to 4; and e is zero or 1.

Indeed the oligomer side chains can themselves be branched, i.e. at each A and L moiety there is the option for branching to occur. Particularly preferred oligomeric polychelants according to the invention include those with a single branching centre, e.g. of formula IV

(IV)

(wherein g is an integer greater than 2; each f is zero or an integer (preferably 1, 2, 3, 4 or 5); each L is independently a linker moiety as hereinbefore defined, (e.g. a substituted or unsubstituted amine-containing hydrocarbon group such as an alkylene, cycloalkylene, alkenylene, alkynylene or arylene group, preferably containing from 1 to 20 carbons and most preferably 1 to 6 carbons (including linear and branched chain groups), a polyalkylamine residue such as —NH($CH_2CH_2NH$—)$_j$ (j being preferably 1 to 20), an aminopolyether residue or an aminopolyalcohol residue (such as an aminopolyethyleneglycol residue) preferably containing from 4 to 20 carbons and most preferably 4 to 8 carbons, an aminocarbohydrate residue, an aminofatty acid residue, or an other suitable group capable of forming an amide or ester linkage with each adjacent chelant moiety A (with any substituting moiety preferably being chosen to enhance solubility or biodistribution of the resultant compound, such as —OH, —$NH_2$ or —$CO_2H$, a peptide residue, a polypeptide or protein such as a plasma protein, antibody or antigen, or other suitable moiety)); each A is independently a chelant moiety; and Z is a multiply-bonding moiety capable of linking the individual oligomer branches enumerated by g to form the oligomeric polychelant.

In particular, the branching site or sites in Z may comprise a multivalent atom such as C, N, B, P or Si as for example in the following branching structures

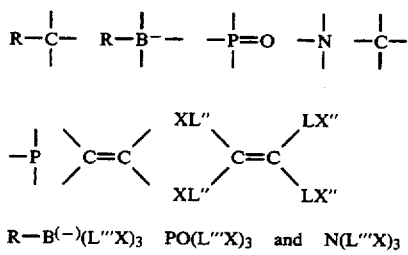

R—B(−)(L'''X)₃    PO(L'''X)₃ and    N(L'''X)₃ where L''' is a portion of the overall linker moiety L, and R is NR'₂ or OR' where each R' which may be the same or different is as defined above; or Z may be a linker moiety of the form L discussed previously.

The A—Z linkages between each branch enumerated by g and the central branching moiety Z may be of an ester-type structure, as for example of the form

[(. . . A'—CO—)O—CH₂CH₂—]$_g$Z ' where g is an integer of 3 or more and Z' is a multivalent branching atom or group, such as N, PO, B, B(−)CH₃ or CCH₃ (for each of which g would be 3).

The A—Z linkages may take the form of amide bonds to a polyamino central linking moiety of the form L. Examples of such structures include compounds of formula II where Z is the residue of a polyamino linker compound such as 1,1,1-tris(aminomethyl)ethane (TAME) or 2,2',2''-triaminotriethylamine. The former may be exemplified by

[(. . . A'—CO—) NH—CH₂—]₃CCH₃ while the latter may be exemplified by

[(. . . A'—CO—)NH—CH₂CH₂—]₃N

It will be appreciated that compounds with more than one branching site will result if Z is a branching moiety linked to four or more chelant moieties and branching from two or more sites in the branching moiety Z. Such structures are exemplified below (see formulae Xa to Xc).

One particularly preferred class of oligomeric polychelants according to the present invention includes those formed from two or more DTPA molecules or derivatives linked by linker moieties to form a single oligomeric molecule. While the following description will frequently refer to compounds and methods related to or utilizing DTPA, it should be understood that other compounds within the scope of the present invention may be formed using other such monochelant molecules, such as DOTA, EDTA, TTHA, TETA, DCTA and the like, and derivatives e.g. esters or amides thereof.

The chelant moieties in the polychelants of the invention are, as already discussed, amide or ester bound to linker moieties. For mid-chain chelant moieties, i.e. those bound to two or more linker moieties, the bulk of the chelant moiety preferably forms part of the oligomer skelton rather than simply being pendant therefrom. Thus it is particularly preferred that where a mid-chain chelant A is the residue of PAPCA the chain between the carbonyls of the amide/ester bonds to at least two of the attached linker moieties should incorporate at least two of the PAPCA amine nitrogens. Similarly for amide-bound linker moieties it is preferred that the body of the linker should contribute to the oligomeric skeleton.

Preferred oligomeric DTPA based polychelants of formula II include those of formula V

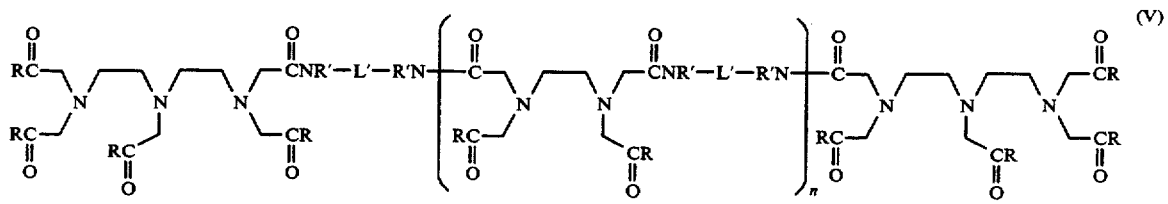

(V)

wherein h is zero or a positive integer (preferably 1, 2, 3, 4 or 5); R is —OR' or —NR₂' where each R' which may be the same or different is as hereinbefore defined; and each L' which may be same or different is a portion of a polyamine linker moiety L as hereinbefore defined.

Particularly preferred polychelants of formula V include those of formula Va

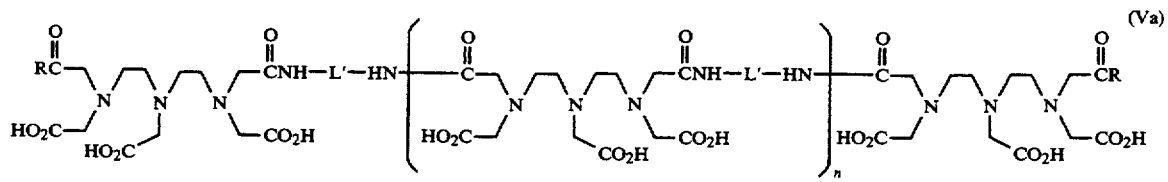

(Va)

where h and L' are as hereinbefore defined and R is as hereinbefore defined other than a hydroxyl group. Such polychelants are, as discussed below, particularly suitable for complexation with M³⁺ metal ions such as Eu³⁺, Gd³⁺, Dy₃₊, Ho³⁺, Yb³⁺ and the like.

For the preparation of the polychelants of the invention, chelant compounds other than, or as well as DTPA may readily be employed, and compounds other than those depicted in formulae V and Va may thus be obtained. For example, the monochelants DOTA, EDTA, TTHA, TETA, DCTA and the like may be substituted for DTPA to yield linear oligomeric polychelants within the scope of formula II. Using a shorthand notation that does not reflect any specific monochelant. Thus for example, isomers of the compounds of formula Va could be produced having the structures

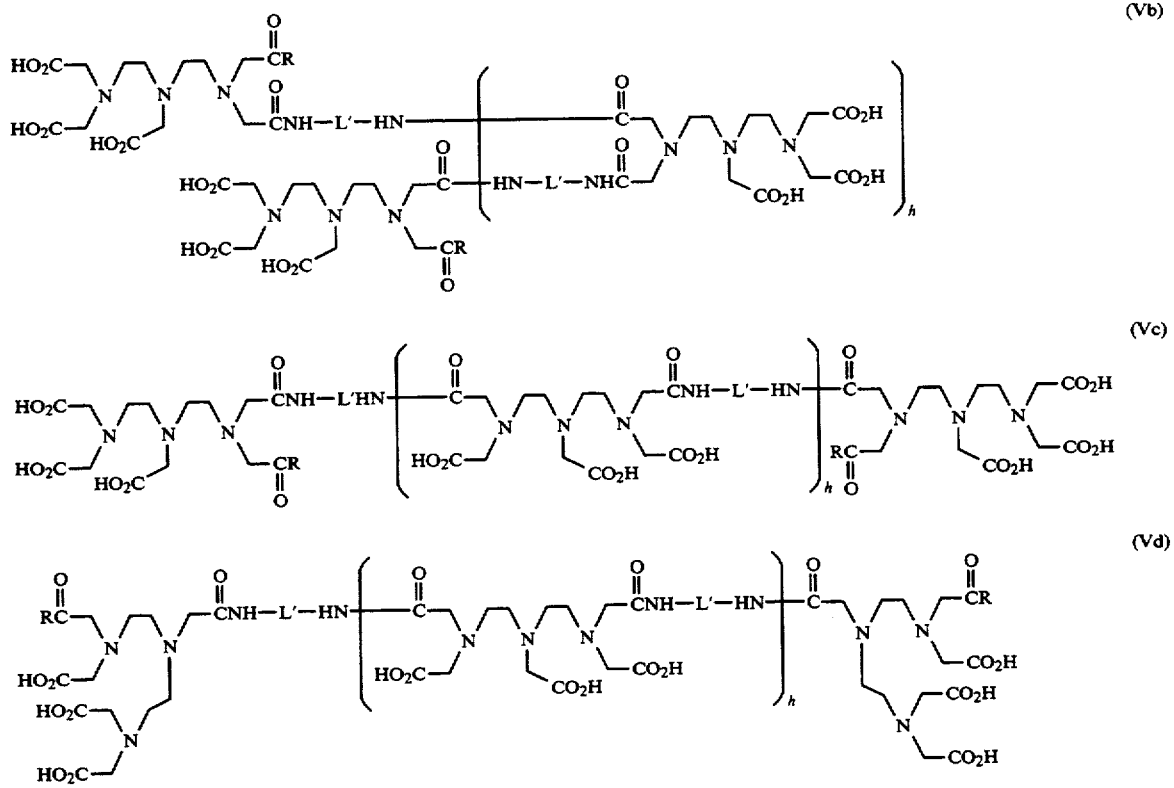

substituents R on the chelant residues, or the specific isomeric form of the oligomeric compounds, formulae V and Va may be rewritten

  (VI)

where each DTPA' is a DTPA residue bound by ester or amide bonds to one or more linker moiety L. Likewise, alternative monochelants such as those listed above may be used to obtain oligomeric polychelants having formulae such as

  (VIIa)

  (VIIb)

  (VIIc)

  (VIId)

It will also be seen that various different isomers may be achieved in oligomeric polychelants such as those of formulae II, V, Va, VI and VIIa to VIId, and the chelates thereof, by bonding linker moieties L to different amide or ester bond-forming moieties on the individual monochelant. Thus for example, isomers of the compounds of formula Va could be produced having the structures or more generally

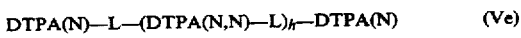  (Ve)

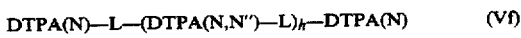  (Vf)

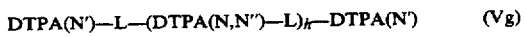  (Vg)

where h, L' and R are as previously defined and where DTPA(N,N") indicates that the DTPA residue is linked via the first and third nitrogens etc. Such compounds may be synthesized using techniques set forth in more detail in the Examples below. Similarly, using the teachings and synthetic methods described herein, various different isomers of compounds such as those of formulae VIIa, VIIb, VIIc and VIId may also be achieved.

As with the linear oligomeric polychelants of formula II, the chelant moieties A incorporated in the branched polychelants, e.g. the compounds of formula IV may preferably comprise one or more ligand groups derived from or related to DTPA. Thus, one preferred class of oligomeric polychelants within the scope of formula IV has the formula VIII

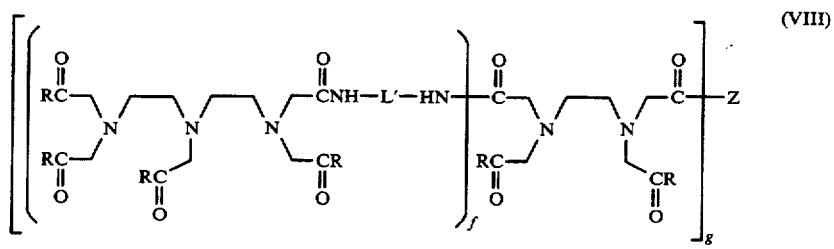

(VIII)

wherein g, R, L', f and Z are as hereinbefore defined.

It is of course possible with the branched oligomeric polychelants to utilize monochelants other than, or as well as, DTPA, including such monochelants as EDTA, TTHA, TETA, DCTA and the like. Structures within the scope of formula IV and analogous to those of shorthand formulae VI and VIIa to VIId may therefore be exemplified as follows:

| | |
|---|---|
| (DOTA'—)$_3$Z | (IXa) |
| [(DOTA'—L—)$_f$DTPA'—]$_3$Z | (IXb) |
| [(TETA'—L—)$_f$DTPA'—]$_3$Z | (IXc) |
| [(EDTA'—L—)$_f$DTPA'—]$_3$Z | (IXd) |
| [(DOTA'—L—)$_f$DOTA'—]$_3$Z | (IXe) |
| (DOTA'—L—)$_4$DOTA' | (IXf) |

As noted above, the branched polychelants may be branched at more than one site—this may be within the same linker moiety or at different linker or chelant moieties. Where branching occurs within the same linker moiety (Z in formulae IV and IXa to IXf) this linker may itself conveniently comprise the residue of a PAPCA, such as DOTA or OTTA for example, and thus the multiply branching linker moiety may have a structure such as

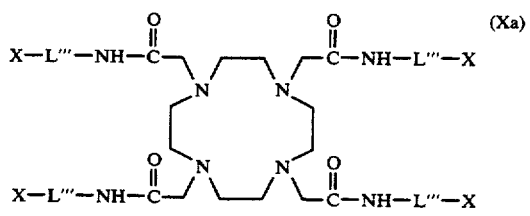

Branching at different linker moieties can be illustrated by structures such as

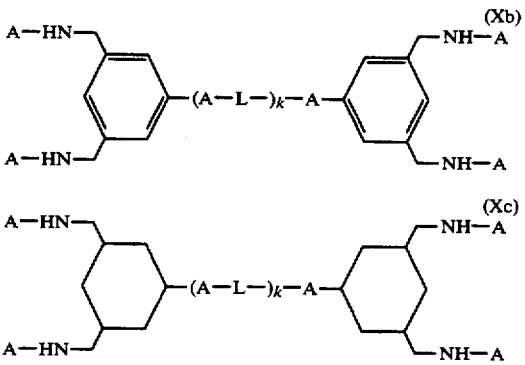

where k is zero or a positive integer.

Using the shorthand notation of, for example, formulae IXa-IXf, the branching section Z or (LA)$_{k+1}$L of formulae Xa-Xc may be used to form oligomeric polychelants such as the following

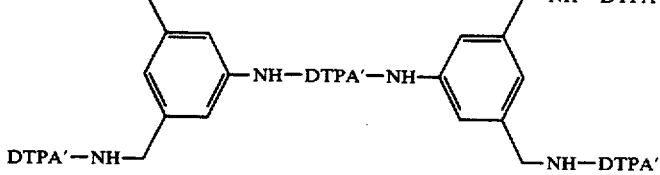
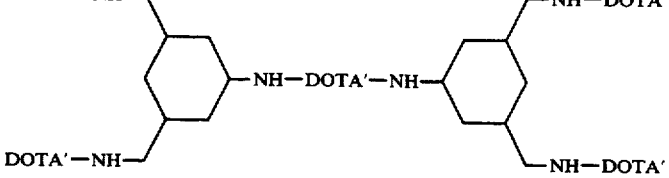

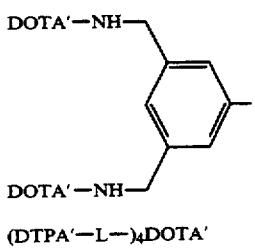

(XIc)

(DTPA′—L—)₄DOTA′    (XId)

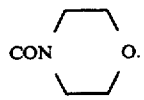

As is the case with the linear structures of formulae V, Va to Vd, VI and VIIa to VIId, different isomeric forms of the branched compounds of, for example, formulae IV, VIII, IXb to IXe and XIa to XIc may be achieved by bonding linker moieties to different sites in the chelant moieties.

In one preferred embodiment of the polychelates of the invention, the net negative charge on the chelant moieties balances or substantially balances the net positive electrical charge on the metal cations chelated by the polychelant whereby the net charge of the polychelate as a whole is low or even zero, so enabling low osmolality compositions of the polychelate to be prepared.

In a particularly preferred embodiment of the present invention, the polychelants comprise at least one chelant moiety that provides a net negative electrical charge sufficient to neutralize the net positive electrical charge on the metal cation associated with that chelant. This eliminates the need to have a salt-forming ion, as for example Na+ or K+ additionally associated with the chelant in order to achieve charge neutrality within that particular chelant metal (A—M) complex, and thereby beneficially decreases the osmolality of the subject compounds and lowers their toxicity. Most preferably, each A—M complex in the oligomeric polychelate will exhibit such charge neutrality.

Thus, for the case of formula Va for example, where a Gd³⁺ ion is associated with each DTPA-derived chelant moiety, charge neutrality may be achieved by selecting as R a substantially non-ionizing substituent group. Suitable R-groups would therefore include those forming a stable amide or ester functionality, as for example where R is N-methylamino, N-methylglucamino, ethoxy, benzoxy, or another alkoxy group stable to hydrolysis under these conditions. Examples of suitable R-groups are disclosed in U.S. Pat. No. A-4,687,658 and 4,687,659.

Particularly conveniently, the polychelants of the invention comprise chelant moieties which are residues of amide derivatives of PAPCAs, for example containing in place of carboxyl moieties groups of formula CONR″₂ where each R″ moiety independently represents hydrogen or a C₁₋₁₈ linear or branched alkyl optionally substituted by one or more hydroxyl or C₁₋₁₆ alkoxy groups or NR″₂ represents a nitrogen-attached 5–8 membered saturated heterocyclic ring optionally containing an oxygen or nitrogen as a further ring heteroatom and optionally substituted by hydroxy, C₁₋₆alkyl or C₁₋₆ alkoxy, for example a group CONHCH₃, CON(CH₃)₂, CONHC₂H₅, CONHCH₂CHOHCH₂OH or This ability to select chelant moieties and substituent groups so as to form low ionic or non-ionic polychelates is a principle that is applicable also to other compounds of the present invention. In particular, it will frequently be advantageous to choose the specific individual monochelant according to the scheme shown in formulae VIIa, VIIb and VIIc such that the net formal charge on each chelant moiety within the oligomeric polychelant is the same. These formulae illustrate examples of equivalent negative charges on each individual chelant moiety so long as each acetic acid moiety among the individual chelant moieties that is not bonded to a linker moiety L is also in the carboxyl form, i.e. is not replaced by a group R— that neutralizes the negative charge of the acetic acid moiety. Alternately, an equivalent formal charge on each chelant moiety in compounds such as those of formula VIId may be obtained where a suitable group R, such as an alkylamino or alkoxy group, as discussed above, replaces one acetic acid moiety of each terminal chelant moiety in the oligomeric polychelant.

As with the polychelants of formula Va, it may be preferable also with respect to branched compounds such as those of formulae VIII, IXa–IXf and XIa–XId to select R-groups bound to the individual chelant moieties so as to achieve at least substantial charge neutrality in the overall polychelate or to achieve charge neutrality in one or more of the complexes between the chelant moieties and the complexed metal ions. Preferably, each such R-group will be selected so as to provide an uncharged complex.

It will also readily be seen in view of the foregoing description that the individual chelant moieties within the oligomeric polychelants of the invention may, as with DTPA, frequently allow substitution in one or more of a variety of positions with groups such as those typified by R in formulae V and VIII. Where a choice of linkage or substitution positions is possible, the particular isomer selected may be dictated by considerations of toxicity, viscosity, solubility, synthetic ease, stability of ligand-metal association, or other considerations. The present invention provides techniques for achieving such varying isomers as will be discussed in more detail below.

Thus, viewed from a further aspect, the invention provides a process for the preparation of a polychelant according to the invention, said process comprising reacting one or more monochelant compounds or derivatives thereof having at least one reactive functional group with one or more linker compounds having at least two functional groups capable of reacting with reactive groups of said monochelants and subsequently if required removing any protecting groups used.

In the process of the invention, the ratios of the quantities of the reagents used will generally correspond to the desired ratios of the chelant and linker moieties of the end product or of the intermediate product if oligomerization is performed in stepwise fashion. The reaction can be performed stepwise or at one time and the product should be periodically sampled to ensure that the desired oligomer is being produced.

In one embodiment, the process of the invention comprises the steps of
(a) obtaining, from a polycarboxylate monochelant starting compound, optionally in carboxylate salt form, an activated polycarboxylate compound containing one or more reactive groups, e.g. imide, amide, anhydride or other activated carboxyl groups;
(b) forming an amide or ester linkage between said activated compound and a polyamine or polyol linking compound thereby to obtain a chelant-linker compound, e.g. using as said linking compound a compound comprising a body portion L' as herein defined and at least two reactive hydroxyl and/or amine groups;
(c) forming an amide or ester linkage between said chelant-linker compound and a second activated polycarboxylate compound to obtain an oligomeric polychelant; and if desired repeating steps (b) and (c) with the product of step (c) to produce a higher oligomeric polychelant.

In this process, one or more of the activated polycarboxylate compounds of steps (a) and (c) may be further substituted at one or more carboxyl moieties with a group of the form R, wherein R is as hereinbefore defined, e.g. a group NR' or OR' where each R' is hydrogen, substituted or unsubstituted alkyl, cycloalkyl or an aromatic (with any substituting moiety being chosen from the group consisting of —OH, —NH$_2$ and —CO$_2$H), or a carbohydrate group, a peptide residue, polypeptide, or a protein.

In the process of the invention one or more of the reactive groups in the reagents, especially on the linking compound, may be protected during the linkage forming step or steps and then subsequently deprotected, e.g. to allow further build up of the oligomeric structure or to allow chelate formation.

The application of the oligomeric polychelants of this invention to medical diagnosis and/or therapy requires in many cases that they be chelated with an appropriate metal or metals. This may be readily accomplished by techniques known to the art (see for example EP-A-292689). Thus for example, the metal to be chelated can be added to water or another liquid medium in the form of an oxide or in the form of an inorganic or organic salt or weak chelate, e.g. a halide or acetate salt, and reacted with an appropriate amount of a polychelant according to the invention or a salt, anhydride or weak complex thereof. The polychelant or salt thereof can be added as an aqueous solution or as a suspension. Heating at temperatures as high as 100° C. for periods up to 48 hours can be utilized depending on the form of the metal and the polychelant used, and their respective concentrations.

Some of the polychelates will be ionic and require counterions. For medical use such counterions should of course be physiologically acceptable. Suitable counterions are well known in the pharmaceutical field and include for example alkali and alkaline earth metal ions such as sodium, potassium, calcium and magnesium as well as organic cations and anions, e.g. ions of organic bases such as ethanolamine, diethanolamine, morpholine, glucamine, N,N-dimethylglucamine, and N-methylglucamine and ions of amino acids or other naturally occurring physiologically tolerable acids. Such polychelate salts may be prepared for example by using a base (for example, an alkali metal hydroxide, meglumine, etc.) to neutralize the polychelates while they are still in solution. Neutral complexes, i.e. those complexes with no formal charge, may require the addition of dilute acid or base to maintain a pH near 7.0. Such neutral complexes are preferred over charged complexes as intravenously administered X-ray and NMR imaging agents because they provide solutions of greater physiologic tolerance due to their lower osmolality.

Thus viewed from another aspect the invention provides a process for producing polychelates according to the invention, said process comprising reacting a polychelant according to the invention, or a salt or weak complex thereof, in a liquid, preferably aqueous, medium with at least one metal compound, preferably an oxide or a compound soluble in water or an organic solvent, e.g. an alkanol, thereby to yield a polychelate containing two or more chelated metal ions per molecule.

Viewed from a further aspect the invention provides the use of a polychelant according to the invention or a salt or chelate thereof for the manufacture of a therapeutic or diagnostic agent for use for example in a method of a diagnostic imaging (e.g. X-ray imaging, MRI, ultrasound imaging, scintigraphy, etc), in radiotherapy or in heavy metal detoxification.

Viewed from a still further aspect the invention also provides a process for the preparation of a diagnostic or therapeutic agent which process comprises admixing a polychelant according to the invention, or a physiologically acceptable salt or chelate thereof, together with at least one pharmaceutical carrier or excipient.

Viewed from another aspect the invention provides a diagnostic or therapeutic composition, e.g. for use in a method of a diagnostic imaging (e.g. X-ray imaging, MRI, ultrasound imaging, scintigraphy, etc), in radiotherapy or in heavy metal detoxification, comprising a polychelant according to the invention or a physiologically acceptable salt or chelate thereof together with at least one pharmaceutical carrier or excipient.

The compositions according to the invention may have a variety of uses, particularly in diagnostic imaging, radiotherapy and heavy metal detoxification. The polychelant, or salt or chelate thereof, contained in the composition will of course be selected according to the desired end use. Thus compositions which are MRI contrast media will contain chelates of the polychelant with at least one paramagnetic metal ion, preferably at least two such ions and especially preferably with one such ion complexed by each chelant moiety within the polychelant. Suitable paramagnetic metal ions have been discussed above but particular mention should be made in this regard to Eu, Ho, Gd, Dy, Mn, Cr and Fe, especially Gd(III), Mn(II) and Dy(III). For such use the paramagnetic metal species is preferably non-radioactive.

Compositions according to the invention which are X-ray or ultrasound contrast media will contain chelates of the polychelant with at least one heavy metal ion (of atomic number greater than 37, preferably greater than 50), preferably at least 2, especially at least 3 such ions and particularly with one such ion complexed by each chelant moiety in the polychelant. The heavy metals may if desired be selected to match their X-ray cross-sections to the .X-ray source to be used in =imaging so as to optimise the contrast enhancement or alternatively the composition may advantageously contain polychelates of more than one heavy metal—either as a mixture of homopolychelates or as a heteropolychelate. Again suitable metals have been discussed above but particular mention may be made of Hf, La, Yb, Dy and Gd, especially Gd(III) and Dy(III). The heavy metal species will of course preferably be non-radioactive.

For use in scintigraphy and radiotherapy, the chelated metal species must of course be radioactive and any conventional complexable radioactive metal may be used, for example radioactive isotopes of Tc, Cu, In, Sm, Ru or Y. For radiotherapy, the polychelates with for example $^{67}$Cu may be used.

For use in detoxification of heavy metals, the polychelant is preferably in salt form with a physiologically acceptable counterion, e.g. sodium, calcium, ammonium, zinc or meglumine.

Viewed from a still further aspect the invention provides a method of generating an image of a human or non-human, preferably mammalian, body said method comprising administering to said body a polychelate according to the invention or a physiologically acceptable salt thereof and generating an image, e.g. an MR, X-ray, ultrasound or scintigraphic image, of at least part of said body, e.g. after permitting sufficient time to elapse for the polychelate to distribute to the desired parts of said body.

Viewed from another aspect the invention provides a method of heavy metal detoxification of a human or nonhuman, preferably mammalian, body said method comprising administering to said body a polychelant according to the invention or a physiologically acceptable salt or weak chelate thereof.

Viewed from a yet further aspect the invention provides a method of radiotherapy of a human or nonhuman, preferably mammalian, body said method comprising administering to said body a radioactive polychelate according to the invention.

Where the polychelate carries an overall charge, such as is the case with the monochelate Gd DTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

The oligomeric polychelates of the invention are administered to patients for imaging in amounts sufficient to yield the desired contrast with the particular imaging technique. Generally dosages of from 0,001 to 5.0 mmoles of chelated contrast-producing ion per kilogram of patient bodyweight are effective to achieve adequate contrast enhancement. For most MRI applications preferred dosages of chelated imaging ion will be in the range from 0.02 to 1.2 mmoles/kg bodyweight while for X-ray applications dosages of from 0.5 to 1.5 mmoles/kg are generally effective to achieve satisfactory X-ray attenuation. Preferred dosages for most X-ray applications are from 0.8 to 1.2 mmoles of the chelated lanthanide or heavy metal/kg bodyweight.

The polychelants/polychelates of the present invention may be formulated with conventional pharmaceutical or veterinary aids, for example stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compositions of the present invention may be in conventional pharmaceutical administration forms such as tablets, capsules, powders, solutions, suspensions, dispersions, syrups, suppositories etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (as for example, DTPA, DTPA-bisamide (e.g. 6-carboxymethyl-3,9-bis(carbamoylmethyl)-3,6,9-triazaundecanedioic acid) or non-complexed oligomeric polychelants) or calcium chelate complexes (as for example calcium DTPA, calcium DTPA-bisamide, Na-CaDTPA-bisamide, calcium oligomeric polychelant or NaCa-oligomeric polychelant), or, optionally, additions (e.g., 1 to 50 mole percent) of calcium or sodium salts (for example, calcium chloride, calcium ascorbate, calcium gluconate or calcium lactate and the like).

If the compounds are to be formulated in suspension form, e.g., in water or physiological saline for oral administration, a small amount of an insoluble polychelant or polychelate may be mixed with one or more of the inactive ingredients traditionally present in oral solutions and/or surfactants and/or aromatics for flavoring..

For MRI and for X-ray imaging of some portions of the body the most preferred mode for administering metal chelates as contrast agents is parenteral, e.g., intravenous administration. Parenterally administerable forms, e.g., intravenous solutions, should be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

The compositions of the invention may also, of course, be in concentrated or dried form for dilution prior to administration.

The present invention will now be illustrated further by the following non-limiting Examples:

EXAMPLE 1

5,8,11-Tris(carboxymethyl)-3-oxo-2,5,8,11-tetraaza-tridecan-13-oic Acid Monohydrate
(DTPA—MMA.H$_2$O)

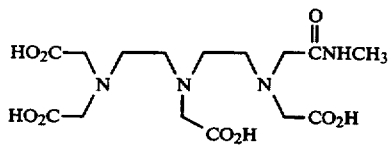

To a 12-L 3-neck round bottom flask equipped with mechanical stirrer, reflux condenser, thermometer, and nitrogen line was added DTPA (1.093 kg, 2.78 mol), anhydrous triethylamine (1.94 L, 13.9 mol), and anhydrous acetonitrile (3.9 L). The mechanically stirred mixture was heated to 60–65° C. under nitrogen for 3 hours after which time virtually all solid dissolved. This solution was cooled to −30° C. and isobutylchloroformate (361 mL, 2.78 mol) was added dropwise over 20 minutes while maintaining the temperature at −30° C. After stirring at −30° C. for 1 hour, 40 wt % aqueous methylamine (2.39 L, 27.8 mol) was added over 5 minutes with stirring. The mixture was allowed to warm to 20°–25° C. After 16 hours stirring was discontinued and the mixture was allowed to separate into two layers. The aqueous (lower) phase was removed by aspiration and concentrated by rotary evaporation (50° C., ca. 1 mm) to a viscous orange gum. The gum was dissolved in 3 L deionized (DI) water, the pH adjusted to 11.0–11.5 with 5N NaOH, and the solution concentrated by rotary evaporation to a white solid. This step was repeated twice to hydrolyze DTPA-isobutyl ester by-products. The solid was dissolved in 1 L DI water and adjusted to pH 6.5 with 12 M HCl. After cooling to 20° C., the solution was loaded onto a 30×100 cm column packed with 22 kg Dowex 1-X8 (acetate, 50–100 mesh). The material was eluted with 30 L DI water, 30 L of 1N, 30 L of 2N, 45 L of 3N, and 45 L of 4N acetic acid (elution by gravity at ca. 325 mL/min; monitored by UV at 254 nm). The product began eluting with late 2N and continued through 4N acetic acid. Fractions (4 L each) were combined on the basis of $^1$H NMR, concentrated by rotary evaporation, and repeatedly reconcentrated with several portions of DI water until acetate free amide was obtained. Lyophilization (10μ, 14 hours) of this material provided 203 g (17% yield) DTPA—MMA.H$_2$O. $^1$H NMR (250 MHz, D$_2$O): δ 2.55 (s, 3H), 6 2.97–3.05 (m, 4H), δ 3.19 (t, 2H, J =6.0 Hz), 6 3.27 (t,2H, J =6.0 Hz), δ 3.46 (s,2H), 6 3.65 (s, 2H), 6 3.75 (s, 6H).

EXAMPLE 2

N-[2-[Bis(carboxymethyl)amino]ethyl]-N-[2-(4-methyl-3,5-dioxo-1-piperazinyl)ethyl]glycine Monohydrate
(DTPA—MMI. H$_2$O )

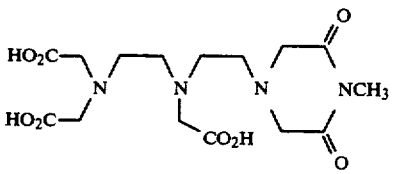

To a 500 mL round bottom flask containing a magnetic stirrer was added DTPA—MMA.H$_2$O (15.0 g, 35.3 mmol) and glacial acetic acid (250 mL). The flask was fitted with a condenser, and the stirred solution was warmed to 80° C. under nitrogen in an oil bath. After 18 hours the reaction mixture was cooled to room temperature, concentrated by rotary evaporation and further dried by high vacuum to an orange yellow solid. The solid was dissolved in 50–100 mL DI water and loaded onto a 14×2.5 inch (35.6×6.4 cm) column packed with Bio-Rad AG1-X8 (acetate, 100–200 mesh). The imide was eluted with 1.0 L DI water followed by 1.0 L each of 1N, 2N, 3N and 4N acetic acid under nitrogen pressure. The product began eluting with early 2N through early 4N acetic acid. Fractions (250–500 mL) were combined on the basis of purity and concentrated by rotary evaporation, and further dried by high vacuum to give 10.95 g (80% yield) DTPA-MMI-H$_2$O. 1H NMR (250 MHz, D$_2$O): δ 2.81 (t, 3H, J =5.4 Hz), δ 2.88(s, 3H), δ 3.14 (t, 2H, J=5.4 Hz), δ 3.27–3.32 (m, 4H), 6 3.48 (s, 4H), 6 3.55 (s, 4H), 6 3.74 (s, 6H).

EXAMPLE 3

15-Amino-3,6-bis(carboxymethyl)-9-[2-(methylamino)-2-oxoethyl-11-oxo-3,6,9,12-tetraazapentadecanoic Acid Monohydrochloride Monohydrate
(DTPA—MA-APA.HCl.H$_2$O)

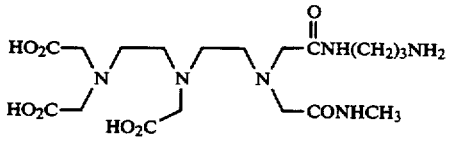

To a 50 mL round bottom flask equipped with magnetic stir bar was added DTPA—MMI.H$_2$O (4.15 g, 10.21 mmol), triethylamine (4.3 mL, 3.0 eq), and methanol (15 mL). The solid dissolved after 5–10 minutes and the flask, under nitrogen, was placed in an ice bath at 5°–10° C. and 1,3diaminopropane (10.2 mL, 12.0 eq) was added in one portion. After 5 minutes the flask was removed from the ice bath and the mixture was stirred for 17 hours at ambient temperature. The solution was concentrated by rotary evaporation to an oily residue which was then dissolved in 25 mL DI water, adjusted to pH 11.5 (5N NaOH), reconcentrated to 10–15 mL, and applied to a 4×2 inch (10.2×5.1 cm) column packed with Bio-Rad AG1-X8 (acetate, 100–200 mesh). The amide was eluted with 300 mL DI water and 600 mL 1N acetic acid. The product was eluted with 1N acetic acid. Fractions (125–250 mL) were combined on the basis of purity, concentrated by rotary evaporation, and further dried under high vacuum to a white solid residue. This solid was dissolved in 25 mL DI water, pH adjusted to 1.8 using 1N HCl (8.9 mL, 1.0 eq), and concentrated to dryness. The residue was dissolved in 25 mL methanol and concentrated to dryness to afford 4.64 g (88% yield) DTPA—MA-APA.HCl.H$_2$O.$^1$H NMR (250 MHz, D$_2$O): δ 1.66 (d, 2H, J=7.2 Hz), δ 2.53(s, 3H), δ 2.78 (t, 2H, J=7.5 Hz), δ 2.98–3.18 (m, 6H), δ 3.23 (t, 2H, J=5.5 Hz), δ 3.36 (t, 2H, J=5.6 Hz), δ 3.44 (s, 2H), δ 3.48 (s, 2H), δ 3.57 (s, 2H), δ 3.72 (s, 4H).

EXAMPLE 4

3,6,22,25-Tetrakis(carboxymethyl)-9,19-bis[2-(methylamino)-2-oxoethyl]-11,17-dioxo-3,6,9,12,16,19,22,25-octaazaheptacosanedioic Acid Dihydrate (propylDTPA-(9,19)BMA-APA.2H$_2$O dimer)

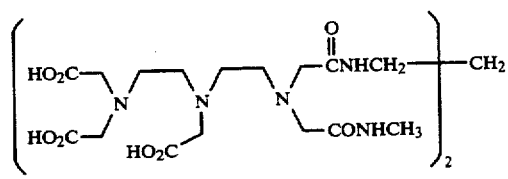

A 25 mL round bottom flask equipped with magnetic stir bar and nitrogen line was charged with DTPA-mono(methyl-propylamine)amide HCl.H$_2$O (0.57 g, 1.1 mmol) and DMSO (2.0 mL). The solid was dissolved with magnetic stirring and anhydrous 1,5-diazabicyclo[4.3.0]non-5-ene (DBN) (1.1 mL, 8.8 mmol) was added followed by 0.25 g 4 Å molecular sieves (2–3 μm powder). To the stirring slurry was added DTPA-mono(methylimide) (0.43 g, 1.10mmol). The mixture was warmed (ca. 35° C.) and then allowed to stir at ambient temperature under nitrogen. After 88 hours the mixture was quenched with 1,3-diaminopropane (1.1 mL, 12.0 eq), stirred 1 hour, diluted with 10 mL methanol and vacuum filtered through a ¼" (0.64 cm) celite bed (medium fritted glass funnel) into a 250 mL round bottom flask containing stirred 1N HCl (8.8 mL). The celite bed was washed with methanol (3×5 mL) and the combined filtrates were concentrated by rotary evaporation to near dryness. The oily residue was dissolved in 25 mL DI water, pH adjusted to 11.5 (5N NaOH), and concentrated by rotary evaporation. Following repeated reconcentration from DI water (2×25 ml), the residue was dissolved in 10 mL DI water, pH adjusted to 8.0 (5N HCl), concentrated to 5–10 mL volume and applied to a 1×7" (2.5×17.8 cm) column bed of Bio-Rad AG1-X8 (acetate, 100–200 mesh). The dimer was eluted with 100 mL DI water, followed by 100 mL of 1N, 2N, 3N, and 4N acetic acid respectively. The product eluted with late 2N through 3N acetic acid. Fractions (50–100 mL) were combined on the basis of purity, concentrated by rotary evaporation, reconcentrated repeatedly from DI water (6×25 ml), and lyophilized (10p, 14hours) to afford 0.18 g (19% yield) PropylD-TPA-(9,19)BMA.2H$_2$O dimer. $^1$H NMR (250 MHz, D$_2$O): δ 1.54 (p, 1H, J=6.4 Hz), δ 2.56 (s, 3H), δ 3.00–3.15 (m, 6H), δ 3.23 (t, 2H, J=5.4 Hz), δ 3.36 (t, 2H, J=5.9 Hz), δ 3.52 (s, 4H), δ 3.57 (s, 2H), δ 3.73 (s, 4H).

Other amidated oligomeric polychelants within the scope of formulae IV and VII may be prepared analogously to Examples L to 4 by using in the procedure of Example 2 starting amides other than the mono- methylamide and by using in the procedure of Example 3 polyamines other than 1,3-diamino-propane. Such polychelants may be chelated with an M$^{3+}$ metal such as Gd$^{3+}$ to achieve useful, nonionic oligomeric polychelates.

EXAMPLE 5

Dimethyl-3,6,9,18,21,24-hexakis(2-methoxy-2-oxoethyl)-11,16-dioxo-3,6,9,12,15,18,21,24-octaazahexacosanedioate (DTPA-Octaester Dimer)

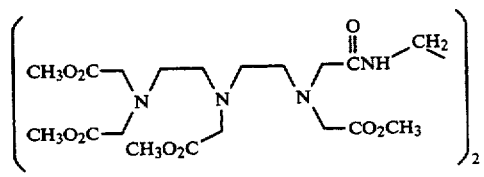

(a) N,N-Bis(2-[bis(2-methoxy-2-oxoethyl)amino]ethyl]glycine methyl ester (DTPA-PMester)

To a stirred suspension of diethylenetriaminepentaacetic acid (100 g, 0,254 mol) in 1 L of absolute methanol was added trimethylorthoformate (200 mL, 1.83 mol). Anhydrous hydrogen chloride was bubbled in at a vigorous rate until the solution began to boil (5–10 minutes). The solution was allowed to boil for 3 hours without using a reflux condenser, and then cooled. Evaporation of the solvents afforded an oil which was diluted with 1 L of saturated, aqueous sodium bicarbonate and extracted with two 400-mL portions of ether. The combined extracts were dried (MgSO$_4$), filtered and evaporated to give 93.0 g (79% yield) of DTPA-PMester as a clear, colorless oil. $^1$H NMR (CDCl$_3$): δ 2.65–2.85 (m, 8H), δ 3.24 (s, 2H), δ 3.32–3.47 (m, 8H), δ 3.54 (s, 3H), δ 3.65 (s, 12H).

(b) N-[2-[Bis(2-methoxy-2-oxoethyl)amino]ethyl]-N-[2-[(carboxymethyl)(2-methoxy-2-oxoethyl)amino]ethyl]-glycine methyl ester, potassium salt (K DTPA-TMester)

To a stirred solution of DTPA-PMester (93.0 g, 0.20 mol ) in 200 mL of absolute methanol was added a solution of 87.8% potassium hydroxide pellets (12.8 g, 0.20 mol) in 50 mL of absolute methanol. The solution was stirred for 15 hours at ambient temperature and the solvent was evaporated. Flash chromatography (SiO$_2$, 0–30% methanol progression in chloroform) gave K+DTPA-TMester (43.8 g, 45% yield) as a colorless oil. R$_f$0.35 (15% MeOH/CHCl$_3$); 1H NMR (CDCl$_3$): δ 2.74 (s, 6H), δ 2.85 (m, 2H), δ 3.35 (s, 2H), δ 3.45 (s, 2H), δ 3.49 (s, 2H), δ 3.53 (s, 4H), δ 3.66 (s, 12H).

(c)

Dimethyl-3,6,9,18,21,24-hexakis(2-methoxy-2-oxoethyl)-11,16-dioxo-3,6,9,12,15,18,21,24-octaazahexacosanedioate (DTPA-Octaester Dimer)

To a stirred solution of K+DTPA-TMester (43.8 g, 0.0898 mol) in 800 mL anhydrous tetrahydrofuran was added dicyclohexylcarbodiimide (18.5 g, 0.0898 mol) and 1-hydroxybenzotriazole (12.1 g, 0.0898 mol). The suspension was stirred for 15 minutes at ambient temperature and ethylenediamine (3.0 mL, 0.0449 mol) was added. After stirring an additional 18 hours at ambient temperature, the suspension was filtered and the solvents were evaporated. The residue was dissolved in 800 mL of ethyl acetate and washed with 800 mL of saturated, aqueous sodium bicarbonate. The organic layer was separated, dried (MgSO4), filtered and evaporated. Flash chromatography (SiO2, 0-5% methanol progression in chloroform) of the residue gave the product (37.2 g, 90% yield) as a clear, light yellow oil. $R_f$ 0.75 (10% MeOH/CHCl3); $^1$H NMR (CDCl3): δ 2.60-2.85 (m, 16H), δ 3.22 (s, 4H), δ 3.34 (t, J=2.5 Hz, 4H), δ 3.41 (s, 8H), δ 3.53 (s, 8H), δ 3.64 (s, 24H), δ 8.00 (br s, 2H).

EXAMPLE 6

3,6,9,18,21,24-Hexakis(carboxymethyl)-11,16-dioxo-3,6,9,12,15,18,21,24-octaazahexacosanedioic Acid (DTPA-Octaacid Dimer)

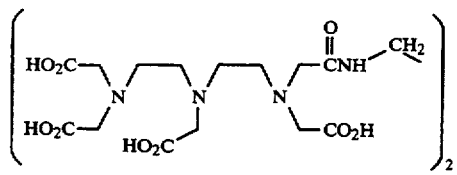

To a stirred solution of DTPA-Octaester dimer (18.3 g, 0.0198 mol) in 100 mL of tetrahydrofuran was added 300 mL of a 1N sodium hydroxide solution. After stirring at ambient temperature for 4 hours, sufficient Bio Rad AG50-X8 resin (100-200 mesh) was added to adjust the pH of the solution to 3.2. The suspension was filtered and the filtrate was evaporated and lyophilized (10μ, 16 hours) to provide the product (14.5 g, 90% yield) as a hygroscopic, light yellow solid of sufficient purity for use in subsequent reactions. 1H NMR (D2O): δ 2.90-3.10 (m, 8H), δ 3.12-3.32 (m, 12H), δ 3.46 (s, 4H), 3.66 (s, 4H), δ 3.75 (s, 12H).

EXAMPLE 7a 3,6,21,24-Tetrakis (carboxymethyl)-9,18-bis[2-(methylamino)-2-oxoethyl]-11,16-dioxo-3,6,9,12,15,18,21,24-octaazahexacosanedioic Acid (EthylDTPA-(9,18)BMA Dimer)

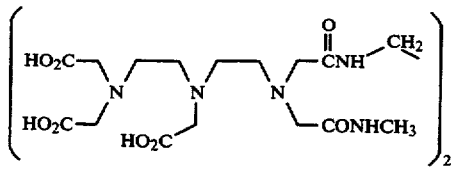

A suspension of DTPA-Octaacid dimer (0.202 g, 0.25 mmol) in 5 mL of glacial acetic acid was heated to 90° C. for 24 hours. The solution was cooled, filtered and evaporated. Then 5 mL of water was added and the solution was evaporated. This was repeated to remove the last traces of acetic acid. The residue, the bis-imide DTPA dimer, was dissolved in 10 mL of 40% aqueous methylamine and stirred at ambient temperature for 1 hour. The solution was evaporated and the residue was purified on Bio-Rad AG1-X8 resin eluting with a 0-4 M acetic acid progression.

The product was evaporated from water three times to remove acetic acid and lyophilized (10μ, 14 hours) to afford the pure product as an off-white solid. 1H NMR (D2O): δ 2.55 (s, 6H), δ 3.00-3.12 (m, 8H), δ 3.17 (s, 4H), δ 3.25 (t, J=5.0 Hz, 4H), δ 3.38 (t, J=5.0 Hz, 4H), δ 3.47 (s, 4H), δ 3.48 (s, 4H), δ 3.57 (s, 4H), δ 3.71 (s, 8H); FAB mass spectrum, m/z: 837 (MH+), 859 (MNa+).

Further chelates can be produced analogously to Examples 5 to 7 by the same general scheme in which two or more equivalents of a polycarboxyl-substituted chelant salt compound (i.e. a polycarboxyl chelant comprising substantially non-ionizing, non-salt Substituted groups on fewer than all of its carboxyl moieties and a salt-forming cation on at least one, and preferably only one, carboxylate moiety) are reacted with a polyamino linker compound to form a polycarboxyl-substituted polychelant. One or more of the substantially non-ionizing substituent groups may thereafter be removed and optionally replaced with an alternate substituent group in one or more positions.

EXAMPLE 7b 3,6,21,24-Tekrakis (carboxymethyl)-9,18-bis[4-(morpholino)-2-oxoethyl]-11,16-dioxo-3,6,9,12,15,18,21,24-octaazahexacosanedioic Acid (EthylDTPA-(9,18)BMO Dimer)

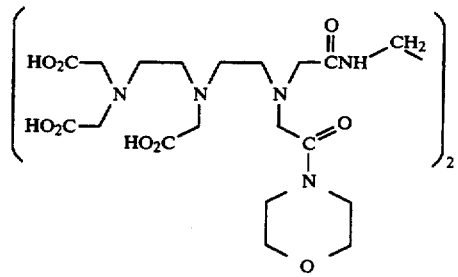

A suspension of DTPA-Octaacid dimer (0,202 g, 0.25 mmol) in 5 mL of galcial acetic acid is heated to 90° C. for 24 hours. The solution is cooled, filtered and evaporated. This is repeated to remove the last traces of acetic acid. The residue, the bis-imide DTPA dimer, is dissolved in 10 mL of morpholine and stirred at ambient temperature for 24 hours. The solution is evaporated and the residue is purified by ion-exchange chromatography followed by lyophilization to afford the title compound.

EXAMPLE 8

6,9,18,21-Tetrakis (carboxymethyl )-3,24-bis[2-(methylamino)-2-oxoethyl]-11,16-dioxo-3,6,9,12,15,18,21,24-octaazahexacosanedioic Acid (EthylDTPA-(3,24)BMA Dimer)

To a stirred solution of DTPA—MMA.H2O (1.0 g, 2.35 mmol) in 30 mL of anhydrous pyridine at 0° C. was added 1,3-dicyclohexylcarbodiimide (DCC) (1.069 g, 5.15 mmol). The ice bath was removed and the mixture allowed to stir for hours at ambient temperature after which time ethylenediamine (78.8 μL, 1.17 mmol) was added. After stirring for 24 hours at ambient temperature, the mixture was stripped to dryness, 10 mL of H2O was added, and the dicyclohexylurea (DCU) precipitate was removed by filtration. After adjusting the pH to 9.0 with 1N NaOH, the solution was applied to a column of AG1-X8 (100-200 mesh, acetate) resin. The product was eluted with 1N acetic acid to yield 0.320 g (33% yield) of the title dimer as a pale yellow solid after acetic acid removal followed by lyophilization. 1H NMR (D2O): δ 2.57 (s, 6H), 3.15-3.45 (m, 20H), δ

3.50–3.70. (m, 20H); FAB mass spectrum, m/z: 837 (MH+).

EXAMPLE 9

6,9,20,23-Tetrakis (carboxymethyl)-3,26-bis [2-(methylamino)-2-oxoethyl]-11,18-dioxo-3,6,9,12,17,20,23,26-octaazaoctacosanedioic Acid (ButylDTPA-(3,26)BMA Dimer)

To a stirred solution of DTPA—MMA.0.43H$_2$O (1.00 g, 2.41 mmol) in 25 mL of anhydrous pyridine was added 1,4-diaminobutane (121 μL, 1.205 mmol). The now cloudy solution was cooled to ice bath temperature and DCC (0.547 g, 2.65 mmol) was added at once. The mixture was stirred for 24 hours at room temperature, stripped to dryness, diluted with 10 mL of water, and the DCU precipitate was removed by filtration. After adjusting the pH from 3.4 to 8.9 with 1N NaOH, the solution was applied to AG1-X8 (100–200 mesh, acetate) resin, and eluted with 1N acetic acid. The pure fractions were combined to give 0.649 g (62% yield) of the title dimer as a white solid after acetic acid removal and lyophilization. $^1$H NMR (D$_2$O): δ 1.28 (br s, 4H), δ 2.52 (s, 6H), δ 2.85–3.20 (m, 20H), δ 3.45–3.65 (m, 20H); FAB mass spectrum, m/z: 865 (MH+).

EXAMPLE 10

6,9,18,21-Tetrakis(carboxymethyl)-12,15-dimethyl-3,24-bis[2-(methylamino)-2-oxoethyl]-11,16-dioxo-3,6,9,12,15,18,21,24-octaazahexacosanedioic Acid (N,N'-dimethylethylDTPA-(3,24)BMA Dimer)

To a stirred solution of DTPA—MMA.0.43 H$_2$O (1.0 g, 2,413 mmol) in 25 mL of anhydrous pyridine was added N,N'-dimethylethylenediamine (128 μL, 1,206 mmol). The cloudy mixture was cooled to ice bath temperature and DCC (0.548 g, 2.654 mmol) was added at once. After stirring for 24 hours at room temperature, the mixture was stripped to dryness, 10 mL of water was added, and the DCU precipitate was removed by filtration. After adjusting the pH to 8.9 with 1N NaOH, the solution was applied to AG1-X8 (100–200 mesh, acetate) resin, and eluted with 1N acetic acid to yield 0,516 g (49% yield) of the title dimer as a white solid after acetic acid removal and lyophilization. $^1$H NMR (D$_2$O): δ 2.56 (s, 6H), δ 2.80 (s, 6H), δ 3.0–3.6 (m, 36H), δ 4.15 (s, 4H); FAB mass spectrum, m/z: 865 (MH+).

EXAMPLE 11

6,9,19,22-Tetrakis (carboxymethyl)-3,25-bis[2-(methylamino)-2-oxoethyl]-11,17-dioxo-3,6,9,12,16,19,22,25-octaazaheptacosanedioic Acid (PropylDTPA-(3,25)BMA Dimer)

To a stirred solution of DTPA—MMA-0.6 H$_2$O (11.61 g, 0.0278 mol) in 650 mL of anhydrous pyridine was added 1,3-diaminopropane (1,030 g, 0.0139 mol). The cloudy mixture was cooled to ice bath temperature and DCC (8.60 g, 0.0417 mol) was added in one portion. After stirring for 20 minutes, the ice bath was removed and the mixture stirred for 48 hours at ambient temperature. The mixture was stripped to dryness, 100 mL of water was added, and the pH adjusted from pH 3.3 to pH 9.0 with 5N NaOH. DCU precipitate was removed by filtration and the solution was applied to AG1-X8 (100–200 mesh, acetate) resin. After three column volumes of water, the dimer product was eluted with 1N acetic acid. The pure fractions were combined to give 5.55 g (47% yield) of the title product after reconcentration three times with water followed by lyophilization. $^1$H NMR (D$_2$O): δ 1.5 (br t, J=9.5 Hz, 4H), δ 2.49 (s, 6H), δ 2.80–3.20 (m, 20H), δ 3.45–3.60 (m, 20H); FAB mass spectrum, m/z: 851 (MH+).

EXAMPLE 12

6,9,19,22-Tetrakis(carboxymethyl)-14-hydroxy-3,25-bis[2-(methylamino)-2-oxoethyl]-11,17-dioxo-3,6,9,12,16,19,22,25-octaazaheptacosanedioic Acid (HOpropylDTPA-(3,25)BMA Dimer)

To a stirred solution of DTPA—MMA.H$_2$O (1.00 g, 2.35 mmol) in 50 mL of anhydrous pyridine at 0° C. was added DCC (1,069 g, 5.15 mmol). The ice bath was removed and the mixture stirred for 3 hours at ambient temperature and 2-hydroxy-1,3-diaminopropane (0.106 g, 1,178 mmol) was added. After stirring for 24 hours at ambient temperature, the mixture was stripped to dryness, 10 mL of water added, and the DCU precipitate removed by filtration. After adjusting the pH from pH 3.4 to pH 9.0 with 1N NaOH, the solution was applied to AG1-X8 (100–200 mesh, acetate) resin, and the product was eluted with 1N acetic acid to yield 0.185 g (18% yield) of the title product as a pale yellow solid after HOAc removal followed by lyophilization. $^1$H NMR (D$_2$O): δ 2.49 (s, 6H), δ 2.95–3.15 (m, 20H), δ 3.40–3.70 (m, 20H); FAB mass spectrum, m/z: 867 (MH+).

EXAMPLE 13

6,9,19,22-Tetrakis(carboxymethyl)-3,26-bis [2-[(2,3-dihydroxypropylamino)-2-oxoethyl]-11,17-dioxo-3,6,9,12,16,19,22,25-octaazaheptacosanedioic Acid (propylDTPA-(3,25)APD Dimer)

To a stirred solution of DTPA—MAPD.1H$_2$O (0.40 g, 0.825 mmol) in 25 mL of anhydrous pyridine at 0° C. was added 1,3-diaminopropane (34 μL, 0,412 mmol). The solution was cooled and DCC (0.187 g, 0.906 mmol) was added. The mixture was stirred for 48 hours at ambient temperature, stripped to dryness, diluted with 10 mL of water, and the DCU removed by filtration. After adjusting the mixture from pH 3.8 to pH 8.9 with 1N NaOH, the solution was applied to AG1-X8 (100–200 mesh, acetate) resin and eluted with 1N acetic acid. The pure fractions were combined to give 0.040 g (10% yield) of the title dimer as an oily solid. 1H NMR (D$_2$O): δ 1.55 (br t, 2H), δ 2.9–3.7 (m, 50H).

The DTpA-mono(2,3-hydroxypropylamide) chelant (DTPAMAPD) used in Example 13 was prepared according to the method of Example 14. Other synthetic methods known to the art may be used to prepare substituted (e.g., amidated or esterified) monomeric chelants that are likewise useful in the synthesis of oligomeric polychelants according to the methods of, for instance, Examples 8–13.

Further polychelants according to the invention can thus be produced by procedures analogous to those of Examples 8 to 13 using different monochelant and polyamino linker compound starting materials.

EXAMPLE 14

3,6,9-Tris (carboxymethyl )-14–15-dihydroxy-11-oxo-3,6,9,12-tetraazapentadecanoic Acid (DTPA—MAPD)

A suspension of DTPA (1.0 g, 2.5 mmol) in 30 mL of DMSO containing triethylamine (1.77 mL, 12.7 mmol) was refluxed until solubilized. The solution was cooled to ambient temperature and 3-amino-1,2-propanediol (0.243 g, mmol) was added, followed by DCC (0.543 g, 2.67 mmol). After stirring for 24 hours, the mixture was stripped to dryness, 10 mL of water was added, and the DCU was removed by filtration. After adjusting the pH from pH 2.9 to pH 8.0 with 1N NaOH, the solution was applied to AG1-X8, acetate resin. The product was eluted with 1N acetic acid. The pure fractions were combined to give 0,409 g (34% yield) of the title compound as a white solid after acetic acid removal and lyophilization. 1H NMR (D2O): δ 2.95–3.40 (m, 12H), δ 3.47 (s, 7H), δ 3.55–3.80 (m 9H); FAB mass spectrum, m/z: 467 (MH+).

EXAMPLE 15

14-Amino-3-[2-[(2-aminoethyl)amino]-2-oxoethyl]-6,9-bis(carboxymethyl)-11-oxo-3,6,9,12-tetraazatetradecanoic Acid Dihydrate (DTPA-B(AE)A.2H2O)

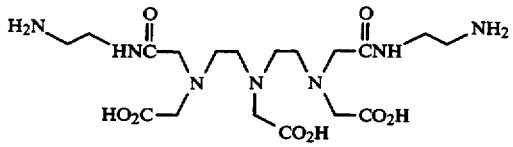

(a) 1,1-Dimethylethyl(2-aminoethyl)carbamate ((tBA)EA)

A 250 mL round bottom flask equipped with magnetic stir bar, addition funnel, and nitrogen line was charged with ethylenediamine (43 mL, 0.65 mol) and chloroform (75 mL). To the stirred solution, cooled in an ice/methanol bath, was added di-t-butyl dicarbonate (21.8g, 0.10 mol) in 30 mL chloroform dropwise over one hour. The reaction mixture was stirred 18 hours at ambient temperature, filtered and concentrated by rotary evaporation to a clear oil. Repeated concentration from toluene (5×50 mL) provided 17 g of a colorless oil. Vacuum distillation of this oil (88°–89° C., ca. 3 mm) gave 12.1 g (76% yield) (t-BA)EA. 1H NMR (250 MHz, CD3Cl): δ 1.12 (s, 2H), δ 1.39 (s, 9H), δ 2.74 (t, 2H, J=5.9 Hz), δ 3.11 (q, 2H, J=5.8 Hz), δ 4.97 (s, 1H).

(b) Bis (1,1-dimethylethyl )-8,11,14-tris (carboxymethyl)-6,16-dioxo-2,5,8,11,14,17,20-heptaazaheneicosanedioate (DTPA-B(tBA)EA)

A 500 mL round bottom flask equipped with magnetic stir bar and nitrogen line was charged with (tBA-)EA (12.08 g, 75.42 mmol), triethylamine (15.0 mL, 107.7 mmol), and acetonitrile (200 mL). To the stirred solution was added DTPA dianhydride (12.83 g, 75.42 mmol) in one portion followed by acetonitrile (50 mL). After 15 minutes the white suspension became a colorless solution. The flask was fitted with a condenser and warmed under nitrogen in an oil bath at 50° C. After 90 hours the reaction mixture was concentrated by rotary evaporation to an off-white solid. This solid was dissolved in 150 mL DI water and concentrated by rotary evaporation to a dry solid. Residual triethylamine was removed by redissolving the solid in 150 mL DI water, adjusting the pH to 10.5 (5 N NaOH), and concentrating by rotary evaporation. 1H NMR (250 MHz, D2O): δ 1.00 (t, 8H, J=7.0 Hz), δ 1.14 (s, 18H), δ 2.86–3.00 (m, 13.4H), δ 3.06 (s, 8H), δ 3.17 (s, 4H), δ 3.32 (s, 4H), δ 3.46 (s, 2H).

(c) 14-Amino-3-[2-[(2-aminoethyl)amino]-2-oxoethyl]-6,9-bis(carboxymethyl)-11-oxo-3,6,9,12-tetraazatetradecanoic Acid Dihydrate (DTPA-B(AE)A)

The DTPA-B(tBA)EA prepared above was dissolved in 110 mL DI water, adjusted to pH 7 (5N HCl), and cooled in an ice bath. To the cool stirred solution was added concentrated HCl (39 mL) in one portion. The mixture was stirred 10 minutes in the ice bath then for 2 hours at ambient temperature. The solution was then cooled in an ice bath, titrated to pH 7 (50% NaOH), and concentrated by rotary evaporation to a dry solid (50 g). A portion of solid NaCl was removed from this material by suspending the solid in 50 mL DI water and vacuum filtering through a medium fritted glass funnel. The filtrate was adjusted to pH 2.5 (5N HCl), concentrated to a 50 mL suspension, and vacuum filtered through a coarse fritted glass funnel to remove additional solid NaCl. The filtrate was loaded onto a 9.5×2.0" (24.1×5.1 cm) column bed of Bio-Rad AG50-X8 (H+, 200–400 mesh). The column was eluted under nitrogen pressure with 0.75 L DI water followed by 1.25 L of 2N ammonium hydroxide. The product eluted with 2N ammonium hydroxide. The UV active fraction was concentrated by rotary evaporation to an oily residue. The residue was dissolved in 100 mL 1N acetic acid, concentrated by rotary evaporation, reconcentrated repeatedly from water (13×100 mL) to remove ammonium acetate, and lyophilized (10μ, 14 hours) to afford DTPA-B(AE)A.2H2O. 1H NMR (250 MHz, D2O/DCl:pH 2.3): δ 2.95 (t, 4H, J=5.7 Hz), δ 3.09–3.28 (b, 8H), δ 3.35 (t, 4H, J=5.7 Hz), δ 3.51 (s, 4H), δ 3.55 (s, 2H), δ 3.66 (s, 4H).

EXAMPLE 16

6,9,18,21,24,33,36-Heptakis(carboxymethyl)-3,39-bis [2-(methylamino)-2-oxoethyl]-11,16,26,31-tetraoxo-3,6,9,12,15,18,21,24,27,30,33,36,39-tridecaazahentetracontanedioic Acid Hexahydrate (EthylDTPA-(3,39)BMA Trimer)

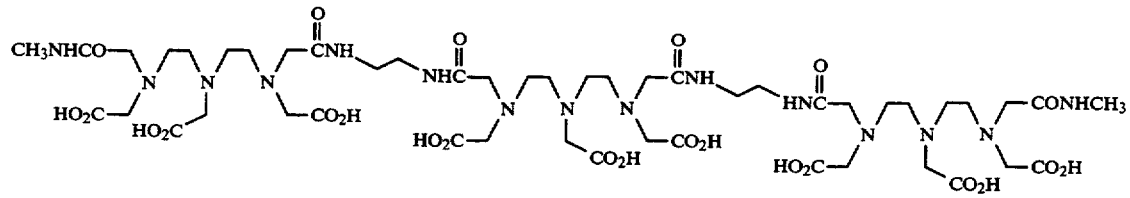

To a 25 mL round bottom flask equipped with magnetic stir bar and nitrogen line was added DTPA-B(A-E)A-2H2O (0.51 g, 1.00 mmol), anhydrous DMSO (3.0 mL), and anhydrous DBN (0.62 mL, 5.0 mmol). The mixture was stirred until all solid dissolved and DTPA-mono(methylamide).H2O (0.85 g, 2.00 mmol) was added. After 5 minutes the solid had dissolved and 1,3-dicyclohexylcarbodiimide (0.45 g, 2.20 mmol) was added. The solution was stirred at ambient temperature, under nitrogen. As the reaction proceeded 1,3-dicyclohexylurea (DCU) appeared as a white precipitate.

After 96 hours the reaction mixture was diluted with acetonitrile (15 mL), vacuum filtered into a 250 mL round bottom flask containing stirred 0.3N HCl (15 mL), and concentrated by rotary evaporation. The residue was dissolved in DI water (25 mL), pH adjusted to 10.5 (1N NaOH), and concentrated by rotary evaporation. DI water (25 mL) was added, and concentration repeated. The residue was dissolved in DI water (20 mL), pH adjusted to 4.5 (1N HCl), refiltered (to remove DCU), and concentrated to 10 mL amber solution. The solution was applied to a 1"×5½" (2.5×14.0 cm) column of Bio-Rex 5 (acetate). The column was eluted under nitrogen with 100 mL DI water followed by 100 mL of 1N, 2N, 3N, 4N, and 5N acetic acid respectively. The trimer eluted with 3N and 4N acetic acid. Fractions were combined on the basis of purity, concentrated by rotary evaporation, reconcentrated repeatedly from water to remove acetic acid (6×25 mL), and lyophilized (10μ, 14 hours) to afford 0.183 g (12% yield) EthylDTPA-(3,39)BMA trimer. $^1$H NMR (250 MHz, $D_2O$): δ 2.56 (s, 6H), δ 3.03-3.26 (m, 32H), δ 3.49-3.60 (m, 18H), δ 3.66 (s, 12H).

Further polychelants comprising more than two chelant moieties can be prepared by procedures analogous to those of Examples 15 and 16 which include the steps of linking a polyanhydride-substituted chelant with two or more (two in the case of a dianhydride ligand) equivalents of a polyamino linker compound, and thereafter using the resultant linker-chelant-linker compound to link with two or more equivalents of another polycarboxylate chelant. Optionally, the polyamino linker compound may be protected at one or more amino positions during the initial linking with the polyanhydride chelant; this procedure will prevent premature reaction and oligomerization at the protected amino position. The protecting group is removed for linking with the other polycarboxylate chelants. The individual chelants may be substituted either prior or subsequent to linkage, e.g. with amide moieties.

EXAMPLE 17

Dimethyl-3,6,9,19,22,25-hexakis(2-methoxy-2-oxoethyl)-14-methyl-11,17-dioxo-14-[5,8,11-tris(2-methoxy-2-oxoethyl)-3,13-dioxo-14-oxa-2,6,8,11-tetraazapentadec-1-yl)-3,6,9,12,16,19,22,25-octaazaheptacosanedioate (TAMEDTPA Dodecaester)

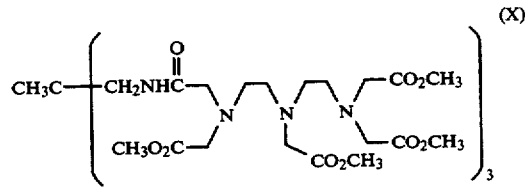

To a stirred mixture of K+DTPA-TMester (46.1 g, 0.095 mol) and dicyclohexylcarbodiimide (19.61 g, 0.095 mol) in dry tetrahydrofuran (800 mL) under nitrogen was added 1-hydroxybenzotriazole hydrate (12.85 g, 0.095 mol). After stirring for 1 hour at 25° C., 1,1,1-tris(aminomethyl)-ethane (3.71 g, 0.0316 mol) was added. After stirring for a further 24 hours, the reaction mixture was filtered. Solvent was removed from the filtrate by evaporation and ethyl acetate (1000 mL) added. Any solid remaining was removed by suction filtration and the filtrate was washed with a saturated solution of sodium bicarbonate (1000 mL), dried ($MgSO_4$) and concentrated in vacuo to a gum. This was chromatographed on silica gel (1000 mL) eluting initially with chloroform and then with a chloroform/methanol mixture, gradually increasing the quantity of methanol up to 10% v/v. This yielded the title product as a thick clear oil (26.8 g; 60% yield). 1H NMR ($CDCl_3$): δ 3.58 (s, 30H), δ 3.55 (s, 6H), δ 3.45 (s, 18H), δ 3.33 (s, 6H), δ 3.22 (s, 6H), δ 2.86-2.89 (d, 6H), δ 2.64-2.70 (m, 24H), δ 0.71 (s, 3H).

EXAMPLE 18

3,6,9,19,22,25-Hexakis(carboxymethyl)-14-[12-carboxy-5,8,11-tris(carboxymethyl)-3-oxo-2,5,8,11-tetraazadodec-1-yl]-14-methyl-11,17-dioxo-3,6,9,1,16,19,22,25-octazaaheptacosanedioic Acid (TAMEDTPA Dodecaacid)

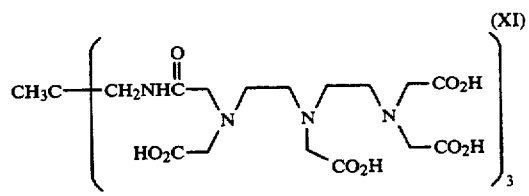

TAMEDTPA dodecaester (1.0 g, 0.71mmol) was dissolved in tetrahydrofuran (8 mL) and 1N sodium hydroxide (17 mL, equiv) was added. After stirring for 15 hours at 25° C., the reaction mixture was concentrated to a solid in vacuo and dissolved in water (2 mL). The solution was adjusted to pH 3.7 by addition of AG 50W-X8 cation exchange resin. After stirring for 15 minutes, the resin was removed by vacuum filtration and the filtrate concentrated to a solid. Lyophilization (10μ, 15 hours) yielded the title product as a white crystalline solid (800 mg; 90%). 1H NMR ($D_2O$): δ 3.63 (s, 18H), δ 3.52 (s, 6H), δ 3.42 (s, 6H), 3.24-3.26 (d, 12H), δ 3.08-3.12 (d, 18H), δ 0.82 (s, 3H).

EXAMPLE 19

6,9,19,22-Tetrakis(carboxymethyl)-14-methyl-3,25-bis[2-(methylamino)-2-oxoethyl]-11,17-dioxo-14-[5,8,11-tris(carboxymethyl)-3,13-dioxo-2,5,8,11,14-pentaazapentadec-1-yl]-3,6,9,12,16,19,22,25-octaazaheptacosanedioic Acid (TAMEDTPA-(3,[11],25)TMA Trimer)

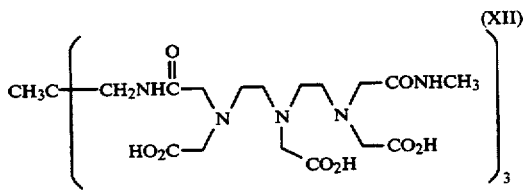

A solution comprising DTPA—MMA.$H_2O$ (Example 1) (1.69 g, 3.9 mmol) and 1,1,1-tris(aminomethyl)ethane (0.1083 g, 0.924 mmol) dissolved in anhydrous pyridine (35 mL) was cooled to 5° C. and dicyclohexylcarbodiimide (1.502 g, 7.28 mmol) was added. After stirring for 50 hours, the pyridine was removed in vacuo and water (10 mL) added to the dry solid. The white precipitate remaining after stirring for 15 minutes was removed by suction filtration and the pale yellow filtrate concentrated to a solid in vacuo and further dried under high vacuum. The solid was dissolved in water (2 mL) and adjusted to pH 4.5 using 1 N sodium hydroxide. Purification on Bio-Rex-5 ion-exchange resin (70 mL) eluting with aqueous acetic acid yielded the product with 3N-4N acetic acid. Fractions containing product were combined and concentrated in vacuo at 50° C. After repeated concentration from water and then lyophilization, the title product was isolated as a white crystalline solid (490 mg; 45% yield). 1H NMR (D₂O): δ 3.75 (s, 6H), δ 3.68 (s, 6H), δ 3.59 (s, 6H), δ 3.58 (s, H), δ 3.1–3.25 (m, 24H), δ 2.97 (s, 6H), δ 2.6 (s, 9H), 0.69.(s, 3H); FAB mass spectrum, m/z: 1283 (MH+).

EXAMPLE 20

6,9,21,24-Tetrakis(carboxymethyl)-3,27-bis[2-(methylamino)-2-oxoethyl]-11,19-dioxo-15-[6,9,12-tris(carboxymethyl)-4,14-dioxo-3,6,9,12,15-pentaazahexadec-1-yl]-3,6,9,12,15,18,21,24,27-nonaazanonacosanedioic Acid (TRENDTPA-(3,[12],27)TMA Trimer)

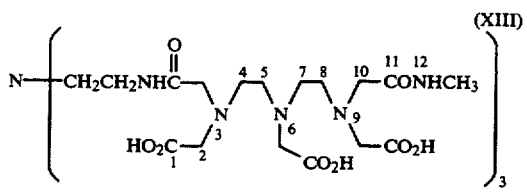

A solution comprising DTPA—MMA.H₂O (Example 1) (1.50 g, 3 59 mmol) and 2,2'2''-triaminotriethylamine (0 117 g, 0,798 mmol) dissolved in anhydrous pyridine (50 mL) was cooled to 5° C. and dicyclohexylcarbodiimide (1,215 g, 5.89 mmol) was added. After stirring for 56 hours, the pyridine was removed in vacuo and water (10 mL) added to the dry solid. The white precipitate remaining after stirring for 15 minutes was removed by suction filtration and the pale yellow filtrate concentrated to a solid in vacuo and further dried under high vacuum. The solid was dissolved in water (2 mL) and adjusted to pH 5.0 using 1N sodium hydroxide. Purification on Bio-Rex-5 ion-exchange resin (70 mL) eluting with aqueous acetic acid yielded the product with 2N acetic acid. Fractions containing product were combined and concentrated in vacuo at 50° C. After repeated concentration from water and then lyophilization, the title product was isolated as a white solid (300 mg; 29% yield). 1H NMR (D₂O): δ 3.4–3.57 (m, H), δ 3.22 (t, 6H), δ 3.13 (s, 12H), δ 3.07 (s, 12H), δ 2.51 (s, 9H); FAB mass spectrum, m/z: 1312 (MH+).

Further branched polychelants of formula VII may be produced analogously to the procedures of Examples 17 to 20 starting with the tetramethyl DTPA potassium salt of Example 5(b).

Oligomeric polychelants comprising mono-chelating groups other than DTPA may of course be prepared using techniques analogous to those described in Examples 1 to 20 above.

EXAMPLE 21

1,11-Bis[4,7,10-tris (carboxymethyl)-1,4,7,10-tetraazacyclododec-1-yl]-2,10-dioxo-6-[(4,7,10-tris(carboxymethyl)-1,4,7,10-tetraazacyclododec-1-yl)-2-oxo-3-azapent-5-yl]-3,6,9-triazaundecane (TREN(DOTA)₃Nonaacid)

a) 1,4,7,10-Tetrakis(2-ethoxy-2-oxoethyl)-1,4,7,10-tetraazacyclododecane (DOTA Tetraethylester)

To DOTA (0,202 g, 0.5 mmol) in a 50 mL round-bottom flask was added 20 mL of saturated ethanolic hydrogen chloride. The mixture was refluxed for 72 hours, cooled and evaporated. The residue was diluted with chloroform and washed with saturated sodium bicarbonate. The organic layer was dried with magnesium sulfate, filtered and evaporated. The crude material was flash chromatographed on silica gel, eluting with a 0–10% methanol-chloroform progression to afford 1,4,7,10-tetrakis(2-ethoxy-2-oxoethyl)-1,4,7,10-tetraazacyclo-dodecane (DOTA Tetraethylester) as a white solid (0.15 g, 58%).

b) 1-Carboxymethyl-4,7,10-tris (2-ethoxy-2-oxoethyl)-1,4,7,10-tetraazacyclododecane, potassium salt (K+DOTA Triethylester)

To DOTA tetraethylester (1.03 g, 2.0 mmol) in 10 mL ethanol is added 87% potassium hydroxide (0,129 g, 2.0 mmol) in 2 mL ethanol. The reaction mixture is stirred for 18 hours and evaporated. The crude material is flash chromatographed on silica gel, eluting with a 0–30% methanol-chloroform progression to afford 1-carboxymethyl-4,7,10-tris (2-ethoxy-2-oxoethyl)-1,4,7,10 -tetraazacyclododecane, potassium salt (K+DOTA Triethylester) as a white solid (0.56 g, 53%).

c) 1,11-Bis[4,7,10-tris(carboxymethyl)-1,4,7,10-tetraazacyclododec-1-yl]-2,10-dioxo-6-[(4,7,10-tris (carboxymethyl)-1,4,7,10-tetraazacyclododec-1-yl)-2-oxo-3-azapent-5-yl]-3,6,9-triazaundecane (TREN (DOTA)₃Nonaacid)

To K+DOTA triethylester (0.526 g, 1.0 mmol ) in 10 mL of anhydrous tetrahydrofuran is added dicyclohexylcarbodiimide (0.206 g, 1.0 mmol) followed by 1-hydroxybenzotriazole (0.135 g, 1.0 mmol). The mixture is stirred for 15 minutes and tris (2-aminoethyl) amine (0.049 g, 0.33 mmol) is added. The reaction mixture is stirred overnight, filtered and concentrated. The residue is diluted with ethyl acetate and washed with saturated sodium bicarbonate. The organic layer is dried with magnesium sulfate, filtered and concentrated. The crude material is flash chromatographed on silica gel, eluting with a 0–20% methanol-chloroform progression to afford the nonaester as a white solid (0.35 g). This is dissolved in 2 mL of tetrahydrofuran and 3 mL of 1.0N NaOH is added and the reaction mixture is stirred overnight. The reaction mixture is purified on Bio-Rad AG1-X8 ion-exchange resin and lyophilized to provide 1,11-bis[4,7,10-tris(carboxymethyl)-1,4,7,10-tetraazacyclododec-1-yl]-2,10-dioxo-6-[(4,7,10-tris (carboxymethyl)-1,4,7,10-tetraazacyclododec-1-yl)-2-oxo-2-azapent-5-yl]-3,6,9-triazaundecane (TREN(DOTA)₃-Nonaacid) (0.18 g) as an off-white solid.

EXAMPLE 22

1,8-Bis[4,7,10-tris(carboxymethyl)-1,4,7,10-tetraazacyclododec-1-yl]-2,7-dioxo-3,6-diazaoctane (EthylDOTA Dimer)

(a)

1,8-Bis[4,7,10-tris(2-ethoxy-2-oxoethyl)-1,4,7,10-tetraazacyclododec-1-yl]-2,7-dioxo-3,6-diazaoctane (EthylDOTA-hexaethylester Dimer)

To a stirred solution of K+DOTA-Triethylester (23.8 g, 0.0453 mol) in 500 mL of anhydrous tetrahydrofuran is added dicyclohexylcarbodiimide (9.33 g, 0.0453 mol) and 1-hydroxybenzotriazole (6.07 g, 0.0453 mol). The suspension is stirred for 15 minutes at ambient temperature and ethylenediamine (1.51 mL, 0.0226 mol) is added. After stirring an additional 24 hours at ambient temperature, the suspension is filtered and the solvents are evaporated. The residue is dissolved in 800 mL of ethyl acetate and is washed with 800 mL of saturated, aqueous sodium bicarbonate. Flash chromatography of the residue affords 18.0 g of EthylDOTA-hexaethylester dimer.

(b)

1,8-Bis[4,7,10-tris(carboxymethyl)-1,4,7,10-tetraazacyclododec-1-yl]-2,7-dioxo-3,6-diazaoctane (EthylDOTA Dimer)

To a stirred solution of EthylDOTA-hexaethylester dimer (15.0 g, 0.0163 mol) in 100 mL of tetrahydrofuran is added 200 mL of a 1N sodium hydroxide solution. After stirring at ambient temperature for 4 hours, sufficient Bio-Rad AG50-X8 resin is added to the solution to adjust the pH to 2.2. The suspension is filtered and the filtrate is evaporated and lyophilized to provide the title product (11.5 g).

Further oligomeric polychelants comprising cyclic linker moieties which may serve as branching sites may be prepared analogously to Examples 21 and 23 using cyclic linker compounds such as DOTA and OTTA derivatives and PAPCA chelants.

EXAMPLE 23

5-Methyl-1,9-bis[4,7,10-tris(carboxymethyl)-1,4,7,10-tetraazacyclododec-1-yl]-2,8-dioxo-5-[(4,7,10-tris(carboxymethyl)-1,4,7,10-tetraazacyclododec-1-yl)-2-oxo-3-azabut-4-yl]-3,7-diazanonane (TAME(DOTA)₃Nonaacid)

[TAME (DOTA)₃ via IBCF Route]

(a) Preparation of DOTA Carboxycarbonic Anhydride.

DOTA (0,808 g, 2.0 mmol) was suspended in 5.0 mL of anhydrous acetonitrile. Tetramethylguanidine (1.00 mL, 8.0 mmol) was added and the reaction mixture was stirred under an atmosphere of nitrogen for about 5 minutes at ambient temperature until the DOTA was dissolved. The resulting solution was cooled to −25° C. under an atmosphere of nitrogen and stirred while adding 0.260 mL (2.0 mmol) of IBCF (isobutylchloroformate), slowly over 5 minutes. The resulting slurry was stirred 1 hour at −25° C.

b)

5-Methyl-1,9-bis[4,7,10-tris(carboxymethyl)-1,4,7,10-tetraazacyclododec-1-yl]-2,8-dioxo-5-[(4,7,10-tris(carboxymethyl)-1,4,7,10-tetraazacyclododec-1-yl)-2-oxo-3-azabut-4-yl]-3,7-diazanonane (TAME (DOTA)₃ Nonaacid)

To the cold slurry from Example 23(a) is added 1,1,1-tris(aminomethyl)ethane (0.039 g, 0.67 mmol) in 2 mL acetonitrile and the mixture is stirred 6 hours at ambient temperature. The mixture is evaporated and purified by ion exchange chromatography on Bio-Rad AG1-X8 resin. Evaporation of the appropriate fraction affords 5-methyl-1,9-bis[4,7,10-tris(carboxymethyl)-1,4,7,10-tetraazacyclododec-1-yl]-2,8-dioxo-5-[(4,7,10-tris (carboxymethyl)-1,4,7,10-tetraaza-cyclododec-1-yl )-2-oxo-3-azabut-4-yl]-3,7-diazanonane (TAME (DOTA)₃ Nonaacid) as a white solid (0.44 g).

EXAMPLE 24

6,9,19,22-Tetrakis(carboxymethyl)-3,25-bis[2-(methylamino)-2-oxoethyl]-11,17-dioxo-14-dimethyl-3,6,9,19,22,25-hexaaza-12,16-dioxahexacosanedioic Acid (2,2-DimethylpropylDTPA-(3,25)BMA Dimer)

To a stirred solution of DTPA—MMA.H₂O (1.0 g, 2.35 mmol) in 30 mL of anhydrous pyridine at 0° C. is added DCC (1.069 g, 5.15 mmol). The ice bath is removed and the mixture allowed to stir for 4 hours at ambient temperature after which time 2,2-dimethyl-1,3-propanediol (0.122g, 1.17mmol) is added. After stirring for 24 hours at ambient temperature, the mixture is stripped to dryness, 10 mL of H₂O is added, and the white DCU precipitate is removed by filtration. Purification on ion-exchange resin followed by lyophilization provides the title dimer.

EXAMPLE 25

6,9,21,24-Tetrakis(carboxymethyl)-3,27-bis[2-(methylamino)-2-oxoethyl]-11,19-dioxo-15-[6,9,12-tris(carboxymethyl)-4,14-dioxo-6,9,12,15-tetraaza-3-oxahexadec-1-yl]-3,6,9,15,21,24,27-heptaaza-12,18-dioxanonocosanedioic Acid. (Triethanolamine Trimer)

A solution containing DTPA—MMA.H₂O (1.50 g, 3.59 mmol) and triethanolamine (0.119 g, 0.798 mmol) dissolved in anhydrous pyridine (50 mL) is cooled to 5° C. and DCC (1.215 g, 5.89 mmol) is added. After stirring for 72 hours, the pyridine is removed in vacuo and water (10 mL) added to the dry solid. The white precipitate of DCU remaining after stirring for 15 minutes is removed by suction filtration and the pale yellow filtrate concentrated to a solid in vacuo and further dried under high vacuum. Purification on ion-exchange resin followed by lyophilization provides the title trimer.

EXAMPLE 26

6,9,19,22-Tetrakis(carboxymethyl)-14-methyl-3,25-bis[2-(methylamino)-2-oxoethyl]-11,17-dioxo-14-[5,8,11-tris(carboxymethyl)-3,13-dioxo-5,8,11,14-tetraaza-2-oxapentadec-1-yl]-3,6,9,19,22,25-hexaaza-12,16-dioxaheptacosanedioic Acid. (THMEDTPA-(3,[11],25)TMA Trimer)

A solution containing DTPA—MMA.H₂O (1.69 g, 3.9 mmol) and 1,1,1-tris(hydroxymethyl)ethane (0.111 g, 0.924 mmol) dissolved in anhydrous pyridine (35 mL) is cooled to 5° C. and DCC (1.502 g, 7.28 mmol) is added. After stirring for 72 hours, the pyridine is removed in vacuo and water (10 mL) added to the dry solid. The white precipitate of DCU remaining after stirring for 15 minutes is removed by filtration. Purification on ion-exchange resin followed by lyophilization provides the title trimer.

EXAMPLE 27

Dy₂(PropylDTPA-(3,25)BMA) Dimer

Method 1

PropylDTPA-(3,25)BMA dimer (636.5 mg, 0.75 mmol) and dysprosium chloride hexahydrate (564.5 mg, 1.50 mmol) are mixed in water at ambient temperature until dissolved. The solution is then adjusted to pH 7 with dilute NaOH.

Method 2

PropylDTPA-(3,25)BMA dimer (3.8 g, 4.29 mmol) and dysprosium oxide (1.6 g, 4.29 mmol) were mixed in 14.3 mL of water and heated to 80° C. for 40 hours. The solution was adjusted to pH 6.7 with dilute NaOH.

EXAMPLE 28

Gd₃EthylDTPA-(3,39)BMA Trimer

EthylDTPA-(3,39)BMA trimer (183 mg, 0.12 mmol) and gadolinium oxide (65.3 mg, 0.18 mmol) are heated at 80° C. until a clear, homogeneous solution is obtained, and then adjusted to pH 7 with dilute NaOH.

EXAMPLE 29

Dy](TAMEDTPA-(3,[11],25)TMA) Trimer

TAMEDTPA-(3,[11],25)TMA trimer (50 mg, 0.039 mmol) and dysprosium acetate tetrahydrate (48.0 mg, 0.117 mmol) are stirred at ambient temperature until homogeneous and adjusted to pH 7 with dilute NaOH.

EXAMPLE 30

Dy₂(PropylDTPA-(9,19)BMA) Dimer

PropylDTPA-(9,19)BMA.H₂O dimer (200 mg, 0.226 mmol) and dysprosium oxide (84.3 mg, 0.226 mmol) were mixed and stirred in 2.3 mL of water and heated to 60° C. for 35 h. The pH was adjusted to 7 with dilute NaOH.

EXAMPLE 31

Hf(IV)₂(DTPA-Octaacid) Dimer DTPA-Octaacid dimer (1.21 g, 1.5 mmol) in 5 mL of water is treated with 1N sodium hydroxide solution (12.0 mL, 12.0 mmol) followed by 0.5M hafnium tetrachloride solution (6.0 mL, 3.0 mmol). The solution is stirred for minutes and adjusted to pH 7 with dilute NaOH.

Although particular examples have been set forth above illustrating various embodiments of the invention, other embodiments will be recognized by the skilled practitioner and may be achieved using techniques known in the art in view of the present disclosure.

We claim:

1. A dichelant comprising two cyclic polyazaalkane chelant moieties, each capable of complexing a metal ion, said moieties being linked together by an amide or ester moiety, and salts and chelates of said dichelant.

2. A dichelant according to claim 1 being a compound of the formula:

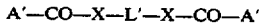

wherein each A'—CO-represents a macrocyclic chelant moiety capable of complexing a metal ion, X—L'—X represents an amide or ester linker moiety in which each X represents oxygen or a secondary, tertiary, or ring nitrogen, and the molecular weight of X—L'—X is less than 1000, and salts and chelates of said dichelant.

3. A dichelant according to claim 2 wherein the bonds between the A'—CO— and X—L'—X moieties are amide bonds, and salts and chelates of said dichelant.

4. A dichelant according to claim 2 wherein the molecular weight of X—L'—X is less than 500, and salts and chelates of said dichelant.

5. A dichelant according to claim 2 wherein the molecular weight of X—L'—X is less than 150, and salts and chelates of said dichelant.

6. A dichelant according to claim 2 wherein X—L'—X provides a chain of 3 to 8 atoms in length between the carbonyl carbon atoms to which the X groups are attached, and salts and chelates of said dichelant.

7. A dichelant according to claim 1 wherein said chelant moieties comprise 1,4,7,10-tetraazacyclododecane-N,N',N"-triacetic acid residues or 1,4,7,10-tetraazacyclododecane -N,N',N",N'"-tetraacetic acid residues, and salts and chelates of said dichelant.

8. 1,8-Bis[4,7,10-tris(carboxymethyl)-1,4,7,10-tetraazacyclododec-1-yl]-27-dioxo-3,6-diazaoctane, and salts and chelates thereof.

9. A dichelate according to claim 1 wherein at least one of said chelant moieties complexes a metal ion.

10. A dichelate according to claim 9 wherein said metal ion is a heavy metal ion, a paramagnetic metal ion or a radioactive metal ion.

11. A dichelate according to claim 10 wherein two of said metal ions are complexed by said chelant moieties.

12. A dichelate according to claim 11 wherein said metal ions are lanthanide metal ions.

13. A dichelate according to claim 12 wherein said metal ions are gadolinium or dysprosium ions.

* * * * *

UNITED STATES PATENT AND TRADEMARK OFFICE
CERTIFICATE OF CORRECTION

PATENT NO. : 5,446,145

DATED : 08/29/95

INVENTORS : David B. Love, William C. Dow, Richard J. Himmelsbach, Alan D. Watson, Scott M. Rocklage It is certified that error appears in the above-identified patent and that said Letters Patent is hereby corrected as shown below:

Col. 2, line 22, change "WO-A5/05554" to --WO-A-85/05554--.

Col. 3, line 42, change "polychelahts" to --polychelants--.

Col. 4, line 22, underline "in vivo"; and line 32, change "metalchelation" to --metal chelation--.

Col. 6, line 44, insert --is-- after "exemplified".

Col. 8, line 12, underline "in vivo".

Col. 9, line 5, delete "20".

Col. 10, line 30, replace formula V with the following formula:

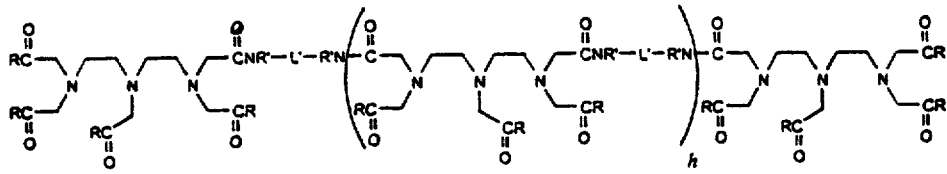

(V)

UNITED STATES PATENT AND TRADEMARK OFFICE
CERTIFICATE OF CORRECTION

PATENT NO.  : 5,446,145

DATED       : August 29, 1995

INVENTOR(S) : David B. Love, William C. Dow,
              Richard J. Himmelsbach, Alan D. Watson, and
              Scott M. Rocklage It is certified that error appears in the above-identified patent and that said Letters Patent is hereby corrected as shown below:

Col. 10, formula Va, change "n" after bracket, to --h--; line 58, change "b" to --h--; and line 62, change "$Dy_{3+}$" to --$Dy^{3+}$--.

Col. 11, line 58, change "(VTTb)" to --(VIIb)--; line 60, change "(VTTC)" to --(VIIc)--.

Col. 13, replace formula VIII, with the following formula:

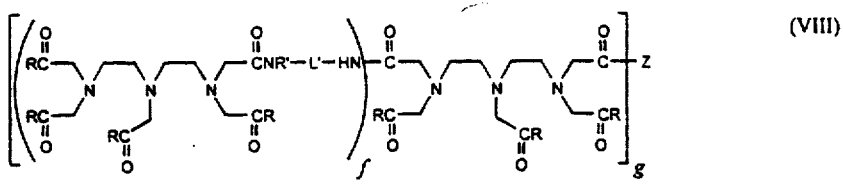

(VIII)

Col. 17, line 36, change "NR'" to -- $NR'_2$ --; line 39, change "$NH_z$" to --$NH_2$--.

Col. 19, line 6, change ".x-ray" to --x-ray--; line 7, change "=imaging" to --imaging--; and line 58, change "0,001" to --0.001--.

Col. 21, line 11, change "$MMA.H_2O$" to --$MMA·H_2O$--; lines 40 and 55, change "ca." to --*ca.*--; line 64, change "$MMA.H_2O$" to --$MMA·H_2O$--; line 65, change "6 2.97" to --$\delta$ 2.97--; lines 66 and 67, change "6 3.27 (t,2H, J =6.0 Hz), $\delta$ 3.46 (s,2H), 6 3.65 (s,2H), 6" to -- $\delta$ 3.27 (t, 2H, J =6.0 Hz), $\delta$ 3.19 (t, 2H, J =6.0 Hz), $\delta$ 3.27 (t, 2H, J =6.0 Hz), $\delta$ 3.46 (s,2H), $\delta$ 3.65 (s, 2H), $\delta$--

UNITED STATES PATENT AND TRADEMARK OFFICE
CERTIFICATE OF CORRECTION

PATENT NO. : 5,446,145

DATED : August 29, 1995

INVENTOR(S) : David B. Love, William C. Dow, Richard J. Himmelsbach, Alan D. Watson, and Scott M. Rocklage It is certified that error appears in the above-identified patent and that said Letters Patent is hereby corrected as shown below:

Col. 22, line 1, change "N" to --N-- in both occurrences; line 3, change "MMI.H$_2$O" to --MMI·H$_2$O--; line 16, change "MMA.H$_2$O" to --MMA·H$_2$O--; line 32, change "MMI.-H$_2$O" to --MMA·H$_2$O--, and change "1H" to --$^1$H--; line 35, change "6 3.48" to --δ 3.48--; change "6 3.55" to --δ 3.55--; and change "6 3.74" to --δ 3.74--; line 41, change "MA-APA.HCl.H$_2$O" to --MA-APA·HCl·H$_2$O--; line 51, change "MMI.H$_2$O" to --MMI·H$_2$O--; and line 55, change "1,3diaminopropane" to --1,3-diaminopropane--.

Col. 23, line 5, change "APA.HCl.H$_2$O" to --APA·HCl·H$_2$O--; line 16 and 17, change "(propylDTPA-(9,19)BMA-APA.2H$_2$O dimer)" to --(PropylDTPA-(9,19)BMA-APA·2H$_2$O dimer)--; line 29, change "HCl. H$_2$O" to --HCI·2H$_2$O--; line 36, change "(ca. 35° C.)" to --(ca. 35° C.)--; line 59, change "(10p, 14hours)" to --(10μ, 14hours)--; line 60, change "BMA.2H$_2$O" to --BMA·2H$_2$O--; and line 67, change "L" to --l--.

Col. 24, line 21, change "N,N" to --N,N--; line 24, change "0,254" to --0.254--; line 40, change "N-[2[Bis(2-methoxy-2-oxoethyl)amino]ethyl]-N" to --N-[2[Bis(2-methoxy-2-oxoethyl)amino]ethyl]-N--; line 42, change "K" to --K$^+$--; line 53, change "1H" to --$^1$H--; line 61, change "K+" to --K$^+$--.

UNITED STATES PATENT AND TRADEMARK OFFICE
CERTIFICATE OF CORRECTION

PATENT NO.  : 5,446,145

DATED       : August 29, 1995

INVENTOR(S) : David B. Love, William C. Dow, Richard J. Himmelsbach, Alan D. Watson, and Scott M. Rocklage It is certified that error appears in the above-identified patent and that said Letters Patent is hereby corrected as shown below:

Col. 25, line 14, change "$2_{1, 24}$" to --21, 24--; line 35, change "1H" to --$^1$H--; and line 37, insert --δ-- before "3.66"; line 66, change "1H" to --$^1$H--.

Col. 26, line 8, change "Substituted" to --substituted--; line 37, change "0,202" to --0.202--; line 53, change "MMA.H$_2$O" to --MMA·H$_2$O--; line 57, insert --4-- before "hours"; and line 68, insert --δ-- before "3.15-3.45".

Col. 27, line 2, change "MH+" to --MH$^+$--; line 9, change "MMA.0.43H$_2$O" to --MMA·0.43H$_2$O--; line 31, change "MMA.0.43H$_2$O" to --MMA·0.43H$_2$O--; line 32, change "2,413" to --2.413--; line 33, change "1,206" to --1.206--; line 42, change "0,516" to --0.516--; line 45, change "MH+" to --MH$^+$--; line 52, change "MMA-0.6H$_2$O" to MMA·0.6H$_2$O; and line 54 change "1,030" to --1.030--.

Col. 28, line 10, change "MMA.H$_2$O" to --MMA·H$_2$O--; line 12, change "1,069" to --1.069--; line 15, change "1,178" to --1.178--; line 32 change "MAPD.1H$_2$O" to --MAPD·1H$_2$O--; line 34, change "0,412" to --0.412--; line 44, change "1H" to --$^1$H--; line 46, change "DTpA" to --DTPA--; and line 67, insert --267-- before "mmol".

Col. 29, line 6, change "0,409" to --0.409--; line 8, change "1H" to --$^1$H--; line 16 change "A.2H$_2$O" to --A·2H$_2$O--; line 38, change "ca" to --_ca_--; and line 39, change "1H" to --$^1$H--; line 40, change "CD3Cl" --CD$_3$Cl--.

UNITED STATES PATENT AND TRADEMARK OFFICE
CERTIFICATE OF CORRECTION

PATENT NO.   : 5,446,145

DATED        : August 29, 1995

INVENTOR(S)  : David B. Love, William C. Dow, Richard J. Himmelsbach, Alan D. Watson, and Scott M. Rocklage It is certified that error appears in the above-identified patent and that said Letters Patent is hereby corrected as shown below:

Col. 30, line 2, change "1H" to --$^1$H--; line 37, change "A.2H$_2$O" to --A·2H$_2$O--; line 60, change "A-2H$_2$O" to --A·2H$_2$O--; and line 63 change ".H$_2$O" to --·H$_2$O--.

Col. 31, line 7, change "added," to --added--; line 56, change "K+" to --K$^+$--; line 68, change "in vacuo" to --in vacuo--.

Col. 32, line 5, change "1H" to --$^1$H--; line 28, insert --25-- before "equiv"; line 30, change "in vacuo" to --in vacuo--; line 36, change "1H" to --$^1$H--; line 39, insert --δ-- before "3.24"; line 57, change "MMA.H$_2$O" to --MMA·H$_2$O--; and lines 62, 63, & 66, change "in vacuo" to --in vacuo--.

Col. 33, line 5, change "in vacuo" to --in vacuo--; line 9, change "1H" to --$^1$H--; line 11, insert --12-- before "H", first occurrence; line 12, insert --δ-- before "0.69"; line 32, change "MMA.H$_2$O" to --MMA·H$_2$O--; line 33, change "3#59" to --3.59--; line 34, change "0117" to --0.117-- and change "0,798" to --0.798--; line 36, change "1,215" to --1.215--; lines 37, 38, 44, & 50, change "in vacuo" to --in vacuo--; line 54, change "1H" to --$^1$H--; and line 55, change "m, H" to --m, 36H--.

UNITED STATES PATENT AND TRADEMARK OFFICE
CERTIFICATE OF CORRECTION

PATENT NO. : 5,446,145

DATED : August 29, 1995

INVENTOR(S) : David B. Love, William C. Dow, Richard J. Himmelsbach, Alan D. Watson, and Scott M. Rocklage It is certified that error appears in the above-identified patent and that said Letters Patent is hereby corrected as shown below:

Col. 34, line 12, change "0,202" to --0.202--; and line 30, change "0,129" to --0.129--.

Col. 35, line 58, change "0,808" to --0.808--.

Col. 36, lines 26 & 44, change "MMA.$H_2O$" to --MMA·$H_2O$--; lines 48, 52, change "in vacuo" to --_in vacuo_--; and line 64, change "MMA.$H_2O$" to --MMA·$H_2O$--.

Col. 37, line 1, change "in vacuo" to --_in vacuo_--; line 30, change "Dy]" to --$Dy_3$--; line 38, change "BMA.$H_2O$" to --BMA·$H_2O$--; line 45 start a new paragraph with --DTPA-Octacid--, second occurrence; and line 50, insert --30-- before "minutes".

Signed and Sealed this

Ninth Day of September, 1997

BRUCE LEHMAN

Attest:

Attesting Officer

Commissioner of Patents and Trademarks